United States Patent [19]
Lewis et al.

[11] Patent Number: 5,955,363
[45] Date of Patent: Sep. 21, 1999

[54] VECTOR FOR IN VITRO MUTAGENESIS AND USE THEREOF

[75] Inventors: Martin K. Lewis, Madison; David V. Thompson, Monona, both of Wis.

[73] Assignee: Promega Corporation, Madison, Wis.

[21] Appl. No.: 08/062,740

[22] Filed: May 17, 1993

Related U.S. Application Data

[63] Continuation of application No. 07/474,630, Jan. 29, 1990, abandoned, which is a continuation-in-part of application No. 07/460,470, Jan. 3, 1990, abandoned.

[51] Int. Cl.$^6$ .................................................. C12K 15/00
[52] U.S. Cl. ...................... 435/440; 435/320.1; 435/471; 435/6; 435/69.1; 435/4; 435/29; 435/34; 435/252.33; 435/91.4; 435/68.1; 435/252.3; 536/23.1; 536/23.4; 536/24.3; 536/23.5
[58] Field of Search .................... 435/6, 69.1, 172.1, 435/172.2, 172.3, 91, 320.1, 317.1, 68.1, 4, 29, 34, 252.33, 440, 471, 91.4, 252.3; 536/23.1, 23.2, 23.4, 23.5, 23.51, 23.52

[56] References Cited

U.S. PATENT DOCUMENTS 4,792,520 12/1988 Stambrook et al. ..................... 435/6

OTHER PUBLICATIONS

Madgwick (1987) Biochem. J. 248:657–662.
Parmley & Smith (1988) Gene 73:305–318.
Ngo et al. 1994 In: The Protein Folding Problem and Tertiary Structure Prediction Merz et al. (eds) Birkhäuser, Boston pp. 433, 492–495.
Hutchinson, et al. 1978, *J. Biol. Chem.*, 253, 6551–6560.
Kramer, et al., 1984, *Cell*, 38,879.
Kramer, et al., 1984 *nucleic Acids Res.*, 12, 9441–9456.
Kunkel, 1985, Proc. *Natl. Acad Sci.*, 82, 488–492.
Kunkel, et al., 1987 *Methods Enzymol.*, 154, 367–382.
Zoller, M.J. and Smith, M., *Method in Enzymology* (1987) vol. 154., 329–351.
Norris, et al., 1983, *Nucleic Acids Res.*, 11, 5103–5113.
Carter, et al., 1985, *Nucleic Acids Res.*, 13, 4431–4443.
Stanssens, et al., 1989, *Nucleic Acids Res.*, 17, 4441–4454.
Vandeyar, et la., 1988, *Gene*, 65, 129–133.
*pGEM Single–strand System Technical Manual* (Jun. 1987, Promega Corporation).
Sutcliffe, J. G., 1979, *Gold Spring Harbor Symp Quant. Biol.*, 43, 77–90.
Peden, K.W.C., 1983, *Gene*, 22, 227–280.

*Primary Examiner*—Lila Feisee
*Assistant Examiner*—Eliane Lazar-Wesley

[57] ABSTRACT

Site-directed in vitro mutagenesis is obtained utilizing a specially-engineered plasmid vector. The vector is engineered to contain an inactivated genetic marker which marker is capable of being reverted to functional expression. Additionally, the vector contains a second genetic marker, a polylinker region and an f1 replication origin.

81 Claims, 15 Drawing Sheets

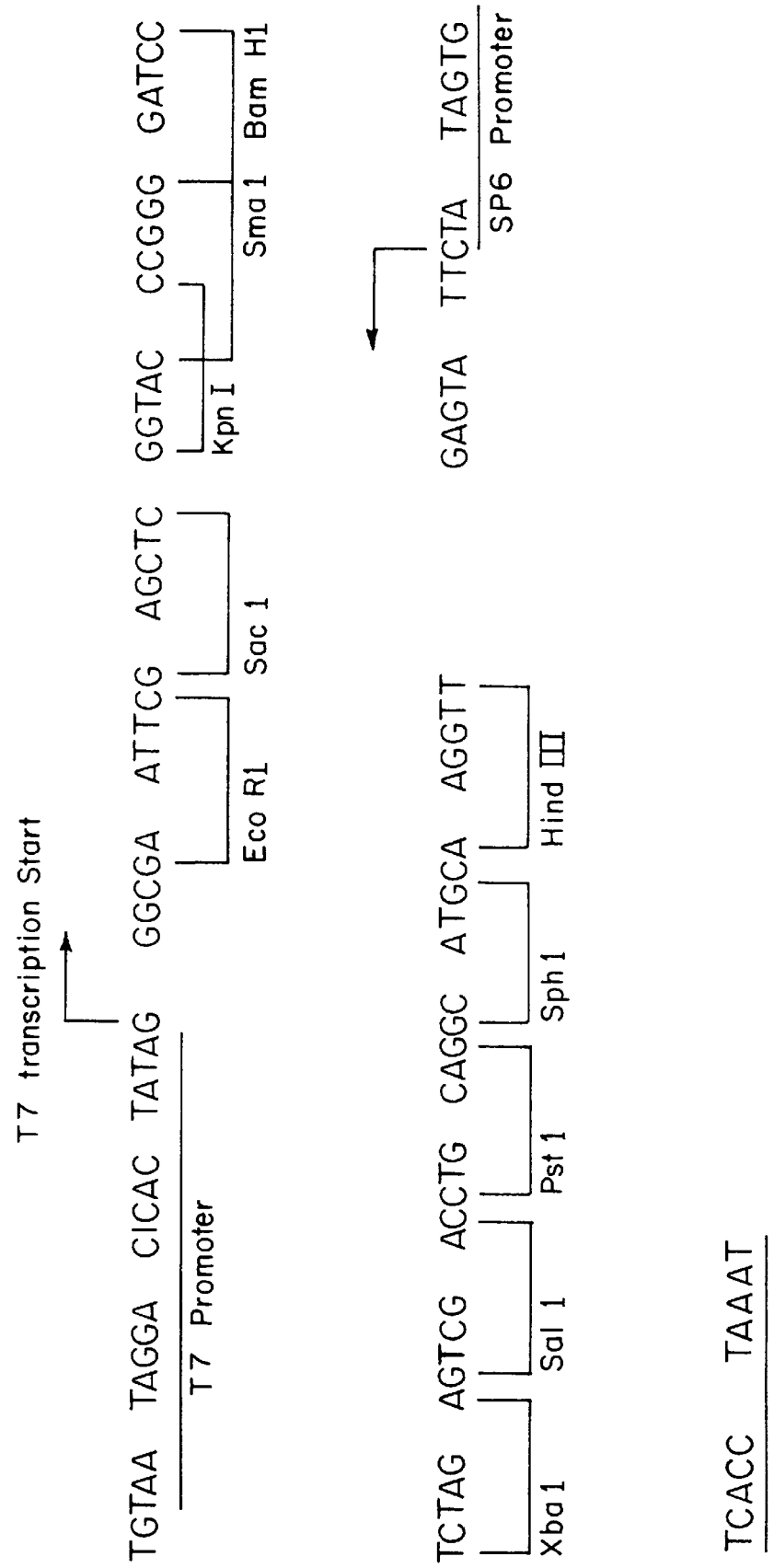
FIG. 2 pSELECT-1 plasmid circle map.

Figure 3. pSELECT-1 plasmid promoter and multiple cloning site sequence. The sequence shown is complementary to the ssDNA produced upon infection with helper phage. This sequence also corresponds to RNA synthesized by T7 RNA polymerase and is complementary to Rna synthesized by SP6 RNA polymerase.

E.     pSELECT-1 Vector Restriction Sites

| Restriction Enzyme | # of Restriction Sites | Position of Cleavage Sites |
| --- | --- | --- |
| Aat II | 1 | 4741 |
| Acc I | 2 | 39, 2702 |
| Acc III | 1 | 2119 |
| Acy I | 6 | 869, 890, 1004, 1661, 4356, 4738 |
| Aha II | 6 | 869, 890, 1004, 1661, 4356, 4738 |
| Alu I | 30 | 13, 58, 88, 110, 205, 269, 387, 471, 486, 1142, 1545, 2455, 2512, 2523, 2572, 2591, 2872, 3098, 3188, 3234, 3491, 4012, 4108, 4171, 4850, 4869, 5099, 5317, 5356, 5570 |
| Apa I | 0 | |
| Asu I | 17 | 627, 979, 1254, 1342, 1591, 1715, 1894, 1936, 2215, 2404, 3865, 3944, 3961, 4179, 4795, 5260, 5548 |
| Ava I | 2 | 21, 1880 |
| Ava II | 8 | 1254, 1342, 1591, 1894, 1936, 2215, 3961, 4179 |
| Bal I | 1 | 1901 |
| BamH I | 1 | 26 |
| Ban I | 12 | 17, 189, 531, 574, 868, 889, 1003, 1221, 1660, 1744, 3771, 5306 |
| Ban II | 4 | 15, 930, 944, 5344 |
| Bbu I | 1 | 54 |
| Bbv I | 27 | 256, 337, 355, 668, 1057, 1240, 1873, 1897, 2001, 2004, 2127, 2510, 2532, 2581, 2678, 2822, 2840, 3259, 3349, 3352, 3558, 3861, 4248, 4859, 5435, 5503, 5576 |
| Bcl I | 0 | |
| Bgl I | 5 | 1390, 1624, 3943, 4063, 5513 |
| Bgl II | 0 | |
| Bsm I | 1 | 1814 |
| BspH I | 4 | 944, 3650, 4654, 4759 |
| BspM I | 2 | 51, 1509 |
| BspM II | 1 | 2119 |
| BssH II | 0 | |
| BstE II | 0 | |
| BstX II | 13 | 316, 931, 1185, 1456, 2048, 2801, 3592, 3663, 4414, 4492, 4601, 5409, 5545 |
| Cfo I | 45 | 229, 294, 322, 355, 558, 690, 718, 871, 892, 952, 1006, 1106, 1158, 1233, 1273, 1404, 1663, 1814, 1876, 1912, 2102, 2185, 2533, 2636, 2666, 2807, 2840, 3110, 3177, 3277, 3451, 3560, 3953, 4046, 4579, 4711, 4811, 4914, 5419, 5427, 5453, 5475, 5484, |

|  |  | 5497, 5521 |
|---|---|---|
| Cfr I | 8 | 284, 750, 854, 986, 1394, 1899, 4207, 5650 |
| Cla I | 1 | 479 |
| Csp45 I | 0 |  |
| Dde I | 9 | 2036, 2198, 2740, 3205, 3614, 3780, 4316, 4742, 4977 |
| Dpn I | 23 | 28, 805, 923, 1282, 1554, 1585, 1600, 1917, 2124, 3498, 3573, 3584, 3592, 3670, 3682, 3787, 4124, 4142, 4188, 4446, 4463, 4499, 5540Dra I |
|  | 3 | 3689, 3708, 4396 |
| Dra II | 4 | 979, 1894, 1936, 4795 |
| Dra III | 1 | 5269 |
| EcoR I | 1 | 5 |
| EcoR V | 1 | 642 |
| Fnu4H I | 53 | 270, 351, 369, 372, 682, 753, 756, 1034, 1037, 1071, 1178, 1229, 1394, 1479, 1562, 1619, 1664, 1743, 1862, 1865, 1872, 1886, 2015, 2018, 2141, 2222, 2521, 2524, 2570, 2667, 2720, 2836, 2854, 2857, 2975, 3130, 3273, 3338, 3341, 3547, 3875, 4064, 4210, 4237, 4332, 4561, 4848, 4957, 5449, 5471, 5485, 5517, 5590 |
| Fok I | 14 | 553, 601, 1455, 1500, 2149, 2211, 2289, 2477, 2618, 3789, 3970, 4253, 4896, 5596 |
| Fsp I | 5 | 717, 1813, 1911, 4045, 5520 |
| Hae II | 15 | 323, 691, 872, 893, 953, 1007, 1107, 1234, 1664, 2103, 2186, 2808, 3178, 5420, 5428 |
| Hae III | 27 | 286, 629, 752, 856, 980, 988, 1052, 1286, 1375, 1396, 1447, 1504, 1717, 1901, 2405, 2945, 2956, 2974, 3408, 3866, 3946, 4209, 4796, 5119, 5261, 5550, 5652 |
| Hga I | 12 | 854, 1408, 1440, 1684, 1834, 2468, 2625, 3041, 3619, 4345, 4903, 5486 |
| HgiA I | 10 | 15, 735, 1046, 1633, 1924, 2750, 3248, 4405, 4490, 4987 |
| Hha I | 45 | 229, 294, 322, 355, 558, 690, 718, 871, 892, 952, 1006, 1106, 1158, 1233, 1273, 1404, 1663, 1814, 1876, 1912, 2102, 2185, 2533, 2636, 2666, 2807, 2840, 3110, 3177, 3277, 3451, 3560, 3953, 4046, 4379, 4711, 4811, 4914, 5419, 5427, 5453, 5475, 5484, 5497, 5521 |
| Hinc II | 2 | 40, 4360 |
| Hind II | 2 | 40, 4360 |
| Hind III | 1 | 56 |
| Hinf I | 18 | 36, 280, 345, 420, 831, 1087, 1307, 1461, 1759, 1980, 2486, 2830, 2905, 3301, 3818, 5196, 5218, 5670 |
| Hpa I | 0 |  |
| Hpa II | 31 | 22, 163, 616, 625, 842, 857, 866, |

| | | 989, 1149, 1225, 1385, 1475, 1713, 1739, 1940, 2120, 2267, 2576, 2610, 3137, 3284, 3310, 3500, 3904, 3938, 4005, 4111, 4353, 4854, 4888, 5371 |
|---|---|---|
| Hph I | 16 | 69, 573, 855, 900, 1754, 1975, 2552, 2561, 3666, 3893, 4305, 4511, 4546, 4830, 4839, 5270 |
| Kpn I | 1 | 21 |
| Mae I | 7 | 33, 685, 1944, 3425, 3678, 4013, 5420 |
| Mae II | 16 | 1356, 1412, 2001, 2025, 2255, 2683, 3633, 4049, 4418, 4738, 5054, 5213, 5225, 5268, 5378, 5636 |
| Mae III | 23 | 75, 579, 667, 1335, 1602, 2262, 2285, 2371, 2584, 2679, 3286, 3349, 3465, 3748, 4075, 4133, 4286, 4474, 4862, 5442, 5454, 5609, 5629 |
| Mbo II | 13 | 316, 931, 1185, 1456, 2048, 2801, 3592, 3663, 4414, 4492, 4601, 5409, 5545 |
| Mlu I | 0 | |
| Mnl I | 31 | 40, 293, 344, 580, 640, 1063, 1244, 1330, 1428, 1632, 1693, 1731, 1758, 1926, 2258, 2316, 2354, 2537, 2567, 2829, 3037, 3112, 3361, 3761, 3842, 3990, 4192, 4785, 4845, 5296, 5561 |
| Msp I | 31 | 22, 163, 616, 625, 842, 857, 866, 989, 1149, 1225, 1385, 1475, 1713, 1739, 1940, 2120, 2267, 2576, 2610, 3137, 3284, 3310, 3500, 3904, 3938, 4005, 4111, 4353, 4854, 4888, 5371 |
| Nae I | 5 | 858, 1226, 1386, 1740, 5372 |
| Nar I | 4 | 869, 890, 1004, 1661 |
| Nci I | 14 | 22, 23, 626, 990, 1714, 1940, 2268, 2576, 2611, 3310, 4006, 4353, 4854, 4889 |
| Nco I | 0 | |
| Nde I | 2 | 2753, 4990 |
| Nhe I | 1 | 684 |
| Nla III | 30 | 54, 103, 449, 463, 810, 948, 1021, 1167, 1206, 1392, 1509, 1637, 1652, 1709, 1916, 2050, 2275, 2339, 2404, 2569, 2674, 2934, 3654, 4141, 4151, 4229, 4265, 4658, 4763, 4847 |
| Nla IV | 29 | 19, 28, 191, 533, 576, 786, 870, 891, 981, 1005, 1223, 1344, 1662, 1711, 1746, 1781, 1895, 1938, 2217, 2962, 3001, 3773, 3867, 3908, 4115, 4705, 5308, 5329, 5341 |
| Not 1 | 0 | |
| Nsi I | 0 | |
| PflM I | 2 | 1776, 1825 |
| PpuM I | 2 | 1894, 1936 |
| Pst I | 1 | 48 |
| Pvu I | 2 | 4189, 5541 |
| Pvu II | 3 | 269, 2523, 5570 |
| Rsa I | 5 | 19, 620, 2738, 4299, 4975 |

| | | |
|---|---|---|
| Sac I | 1 | 15 |
| Sac II | 0 | |
| Sal I | 1 | 38 |
| Sau3A I | 23 | 26, 803, 921, 1280, 1552, 1583, 1598, 1915, 2122, 3496, 3571, 3582, 3590, 3668, 3680, 3785, 4122, 4140, 4186, 4444, 4461, 4497, 5538 |
| Sau96 I | 17 | 627, 979, 1254, 1342, 1591, 1715, 1894, 1936, 2215, 2404, 3865, 3944, 3961, 4179, 4795, 5260, 5548 |
| Sca I | 1 | 4299ScrF I |
| | 22 | 22,23, 185, 586, 626, 990, 1515, 1714, 1898, 1940, 2268, 2576, 2611, 2958, 3079, 3092, 3310, 4006, 4353, 4854, 4889, 5617 |
| SfaN I | 26 | 579, 668, 692, 857, 869, 1103, 1478, 1490, 1885, 2127, 2137, 2233, 2311, 2374, 2596, 2731, 2767, 2807, 3027, 4075, 4266, 4515, 4874, 4968, 5004, 5044 |
| Sfi I | 0 | |
| Sin I | 8 | 1254, 1342, 1591, 1894, 1936, 2215, 3961, 4179 |
| Sma I | 1 | 23 |
| Spe I | 0 | |
| Sph I | 1 | 54 |
| Spo I | 0 | |
| Ssp I | 3 | 4623, 5061, 5085 |
| Stu I | 0 | |
| Sty I | 1 | 1824 |
| Taq I | 9 | 9, 39, 479, 794, 1582, 1723, 3030, 4470, 5302 |
| Tha I | 32 | 292, 294, 802, 1158, 1273, 1402, 1429, 1434, 1495, 1561, 1690, 1700, 1845, 1871, 1993, 2090, 2462, 2531, 2533, 2636, 2977, 3558, 3888, 4377, 4709, 4809, 4811, 4914, 5077, 5453, 5473, 5497 |
| Tth111 I | 1 | 2677 |
| Xba I | 1 | 32 |
| Xho I | 0 | |
| Xho II | 8 | 26, 2122, 3571, 3582, 3668, 3680, 4444, 4461 |
| Xma I | 1 | 21 |
| Xma III | 1 | 1394 |

Enzymes that do not cut the pSELECT-1 vector:

| Apa I | Bcl I | Bgl II | BssH II | BstE II | Csp45 I | Hpa I | Mlu I | Nco I |
|---|---|---|---|---|---|---|---|---|
| Not I | Nsi I | Sac II | Sfi I | Spe I | Spo I | Stu I | Xho I | |

Figure 4:

pSELECT-1 Vector Sequence

| 1 | GGGCGAATTC | GAGCTCGGTA | CCCGGGGATC | CTCTAGAGTC | GACCTGCAGG |
|---|---|---|---|---|---|
| 51 | CATGCAAGC | TGAGTATTCT | ATAGTGTCAC | CTAAATAGCT | TGGCGTAATC |
| 101 | ATGGTCATAG | CTGTTTCCTG | TGTGAAATTG | TTATCCGCTC | ACAATTCCAC |
| 151 | ACAACATACG | AGCCGGAAGC | ATAAAGTGTA | AAGCCTGGGG | TGCCTAATGA |
| 201 | GTGAGCTAAC | CACATTAAT | TGCGTTGCGC | TCACTGCCCG | CTTTCCAGTC |
| 251 | GGGAAACCTG | TCGTGCCAGC | TGCATTAATG | AATCGGCCAA | CGCGCGGGGA |
| 301 | GAGGCGGTTT | GCGTATTGGG | CGCTCTTCCG | CTTCCTCGCT | CACTGACTCG |
| 351 | CTGCGCTCGG | TCGTTCGGCT | GCGGCGAGCG | GTATCAGCTC | ACTCAAAGGC |
| 401 | GGTAATACGG | TTATCCACAG | AATCAGGGGA | TAACGCAGGA | AAGAACATGA |
| 451 | ATTAATTCTC | ATGTTTGACA | GCTTATCATC | GATTAGCTTT | AATGCGGTAG |
| 501 | TTTATCACAG | TTAAATTGCT | AACGCAGTCA | GGCACCGTGT | ATGAAATCTA |
| 551 | ACAATGCGCT | CATCGTCATC | CTCGGCACCG | TCACCCTGGA | TGCTGTAGGC |
| 601 | ATAGGCTTGG | TTATGCCGGT | ACTGCCGGGC | CTCTTGCGGG | ATATCGTCCA |
| 651 | TTCCGACAGC | ATCGCCAGTC | ACTATGGCGT | GCTGCTAGCG | CTATATGCGT |
| 701 | TGATGCAATT | TCTATGCGCA | CCCGTTCTCG | GAGCACTGTC | CGACCGCTTT |
| 751 | GGCCGCCGCC | CAGTCCTGCT | CGCTTCGCTA | CTTGGAGCCA | CTATCGACTA |
| 801 | CGCGATCATG | GCGACCACAC | CCGTCCTGTG | GATTCTCTAC | GCCGGACGCA |
| 851 | TCGTGGCCGG | CATCACCGGC | GCCACAGGTG | CGGTTGCTGG | CGCCTATATC |
| 901 | GCCGACATCA | CCGATGGGGA | AGATCGGGCT | CGCCACTTCG | GGCTCATGAG |
| 951 | CGCTTGTTTC | GGCGTGGGTA | TGGTGGCAGG | CCCCGTGGCC | GGGGGACTGT |
| 1001 | TGGGCGCCAT | CTCCTTACAT | GCACCATTCC | TTGCGGCGGC | GGTGCTCAAC |
| 1051 | GGCCTCAACC | TACTACTGGG | CTGCTTCCTA | ATGCAGGAGT | CGCATAAGGG |
| 1101 | AGAGCGCCGA | CCGATGCCCT | TGAGAGCCTT | CAACCCAGTC | AGCTCCTTCC |
| 1151 | GGTGGGCGCG | GGCATGACT | ATCGTCGCCG | CACTTATGAC | TGTCTTCTTT |
| 1201 | ATCATGCAAC | TCGTAGGACA | GGTGCCGGCA | GCGCTCTGGG | TCATTTTCGG |
| 1251 | CGAGGACCGC | TTTCGCTGGA | GCGCGACGAT | GATCGGCCTG | TCGCTTGCGG |
| 1301 | TATTCGGAAT | CTTGCACGCC | CTCGCTCAAG | CCTTCGTCAC | TGGTCCCGCC |
| 1351 | ACCAAACGTT | TCGGCGAGAA | GCAGGCCATT | ATCGCCGGCA | TGGCGGCCGA |
| 1401 | CGCGCTGGGC | TACGTCTTGC | TGGCGTTCGC | GACGCGAGGC | TGGATGGCCT |
| 1451 | TCCCCATTAT | GATTCTTCTC | GCTTCCGGCG | GCATCGGGAT | GCCCGCGTTG |
| 1501 | CAGGCCATGC | TGTCCAGGCA | GGTAGATGAC | GACCATCAGG | GACAGCTTCA |

| 1551 | AGGATCGCTC | GCGGCTCTTA | CCAGCCTAAC | TTCGATCACT | GGACCGCTGA |
|------|------------|------------|------------|------------|------------|
| 1601 | TCGTCACGGC | GATTTATGCC | GCCTCGGCGA | GCACATGGAA | CGGGTTGGCA |
| 1651 | TGGATTGTAG | GCGCCGCCCT | ATACCTTGTC | TGCCTCCCCG | CGTTGCGTCG |
| 1701 | CGGTGCATGG | AGCCGGGCCA | CCTCGACCTG | AATGGAAGCC | GGCGGCACCT |
| 1751 | CGCTAACGGA | TTCACCACTC | CAAGAATTGG | AGCCAATCAA | TTCTTGCGGA |
| 1801 | GAACTGTGAA | TGCGCAAACC | AACCCTTGGC | AGAACATATC | CATCGCGTCC |
| 1851 | GCCATCTCCA | GCAGCCGCAC | GCGGCGCATC | TCGGGCAGCG | TTGGGTCCTG |
| 1901 | GCCACGGGTG | CGCATGATCG | TGCTCCTGTC | GTTGAGGACC | CGGCTAGGCT |
| 1951 | GGCGGGGTTG | CCTTACTGGT | TAGCAGAATG | AATCACCGAT | ACGCGAGCGA |
| 2001 | ACGTGAAGCG | ACTGCTGCTG | CAAAACGTCT | GCGACCTGAG | CAACAACATG |
| 2051 | AATGGTCTTC | GGTTTCCGTG | TTTCGTAAAG | TCTGGAAACG | CGGAAGTCAG |
| 2101 | CGCCCTGCAC | CATTATGTTC | CGGATCTGCA | TCGCAGGATG | CTGCTGGCTA |
| 2151 | CCCTGTGGAA | CACCTACATC | TGTATTAACG | AAGCGCTGGC | ATTGACCCTG |
| 2201 | AGTGATTTTT | CTCTGGTCCC | GCCGCATCCA | TACCGCCAGT | TGTTTACCCT |
| 2251 | CACAACGTTC | CAGTAACCGG | GCATGTTCAT | CATCAGTAAC | CCGTATCGTG |
| 2301 | AGCATCCTCT | TCGTTTCAT | CGGTATCATT | ACCCCCATGA | ACAGAAATTC |
| 2351 | CCCTTACAC | GGAGGCATCA | AGTGACCAAA | CAGGAAAAAA | CCGCCCTTAA |
| 2401 | CATGGCCCGC | TTTATCAGAA | GCCAGACATT | AACGCTTCTG | GAGAAACTCA |
| 2451 | ACGAGCTGGA | CGCGGATGAA | CAGGCAGACA | TCTGTGAATC | GCTTCACGAC |
| 2501 | CACGCTGATG | AGCTTTACCG | CAGCTGCCTC | GCGCGTTTCG | GTGATGACGG |
| 2551 | TGAAAACCTC | TGACACATGC | AGCTCCCGGA | GACGGTCACA | GCTTGTCTGT |
| 2601 | AAGCGGATGC | CGGGAGCAGA | CAAGCCCGTC | AGGGCGCGTC | AGCGGGTGTT |
| 2651 | GGCGGGTGTC | GGGGCGCAGC | CATGACCCAG | TCACGTAGCG | ATAGCGGAGT |
| 2701 | GTATACTGGC | TTAACTATGC | GGCATCAGAG | CAGATTGTAC | TGAGAGTGCA |
| 2751 | CCATATGCGG | TGTGAAATAC | CGCACAGATG | CGTAAGGAGA | AAATACCGCA |
| 2801 | TCAGGCGCTC | TTCCGCTTCC | TCGCTCACTG | ACTCGCTGCG | CTCGGTCGTT |
| 2851 | CGGCTGCGGC | GAGCGGTATC | AGCTCACTCA | AAGGCGGTAA | TACGGTTATC |
| 2901 | CACAGAATCA | GGGGATAACG | CAGGAAAGAA | CATGTGAGCA | AAAGGCCAGC |
| 2951 | AAAAGGCCAG | GAACCGTAAA | AAGGCCGCGT | TGCTGGCGTT | TTTCCATAGG |
| 3001 | CTCCGCCCCC | CTGACGAGCA | TCACAAAAAT | CGACGCTCAA | GTCAGAGGTG |
| 3051 | GCGAAACCCG | ACAGGACTAT | AAAGATACCA | GGCGTTTCCC | CCTGGAAGCT |
| 3101 | CCCTCGTGCG | CTCTCCTGTT | CCGACCCTGC | CGCTTACCGG | ATACCTGTCC |
| 3151 | GCCTTTCTC | CTTCGGGAAG | CGTGGCGCTT | TCTCATAGCT | CACGCTGTAG |

| 3201 | GTATCTCAGT | TCGGTGTAGG | TCGTTCGCTC | CAAGCTGGGC | TGTGTGCACG |
|---|---|---|---|---|---|
| 3251 | AACCCCCCGT | TCAGCCCGAC | CGCTGCGCCT | TATCCGGTAA | CTATCGTCTT |
| 3301 | GAGTCCAACC | CGGTAAGACA | CGACTTATCG | CCACTGGCAG | CAGCCACTGG |
| 3351 | TAACAGGATT | AGCAGAGCGA | GGTATGTAGG | CGGTGCTACA | GAGTTCTTGA |
| 3401 | AGTGGTGGCC | TAACTACGGC | TACACTAGAA | GGACAGTATT | TGGTATCTGC |
| 3451 | GCTCTGCTGA | AGCCAGTTAC | CTTCGGAAAA | AGAGTTGGTA | GCTCTTGATC |
| 3501 | CGGCAAACAA | ACCACCGCTG | GTAGCGGTGG | TTTTTTTGTT | TGCAAGCAGC |
| 3551 | AGATTACGCG | CAGAAAAAAA | GGATCTCAAG | AAGATCCTTT | GATCTTTTCT |
| 3601 | ACGGGGTCTG | ACGCTCAGTG | GAACGAAAAC | TCACGTTAAG | GGATTTTGGT |
| 3651 | CATGAGATTA | TCAAAAGGA | TCTTCACCTA | GATCCTTTTA | AATTAAAAAT |
| 3701 | GAAGTTTTAA | ATCAATCTAA | AGTATATATG | AGTAAACTTT | GGCTGACAGT |
| 3751 | TACCAATGCT | TAATCAGTGA | GGCACCTATC | TCAGCGATCT | GTCTATTTCG |
| 3801 | TTCATCCATA | GTTGCCTGAC | TCCCCGTCGT | GTAGATAACT | ACGATACGGG |
| 3851 | AGGGCTTACC | ATCTGGCCCC | AGTGCTGCAA | TGATACCGCG | AGACCCACGC |
| 3901 | TCACCGGCTC | CAGATTTATC | AGCAATAAAC | CAGCCAGCCG | GAAGGGCCGA |
| 3951 | GCGCAGAAGT | GGTCCTGCAA | CTTTATCCGC | CTCCATCCAG | TCTATTAATT |
| 4001 | GTTGCCGGGA | AGCTAGAGTA | AGTAGTTCGC | CAGTTAATAG | TTTGCGCAAC |
| 4051 | GTTGTTGCCA | TTGCGGCATC | GTGGTGTCAC | GCTCGTCGTT | TGGTATGGCT |
| 4101 | TCATTCAGCT | CCGGTTCCCA | ACGATCAAGG | CGAGTTACAT | GATCCCCCAT |
| 4151 | GTTGTGCAAA | AAAGCGGTTA | GCTCCTTCGG | TCCTCCGATC | GTTGTCAGAA |
| 4201 | GTAAGTTGGC | CGCAGTGTTA | TCACTCATGG | TTATGGCAGC | ACTGCATAAT |
| 4251 | TCTCTTACTG | TCATGCCATC | CGTAAGATGC | TTTTCTGTGA | CTGGTGAGTA |
| 4301 | CTCAACCAAG | TCATTCTGAG | AATAGTGTAT | GCGGCGACCG | AGTTGCTCTT |
| 4351 | GCCCGGCGTC | AACACGGGAT | AATACCGCGC | CACATAGCAG | AACTTTAAAA |
| 4401 | GTGCTCATCA | TTGGAAAACG | TTCTTCGGGG | CGAAAACTCT | CAAGGATCTT |
| 4451 | ACCGCTGTTG | AGATCCAGTT | CGATGTAACC | CACTCGTGCA | CCCAACTGAT |
| 4501 | CTTCAGCATC | TTTTACTTTC | ACCAGCGTTT | CTGGGTGAGC | AAAAACAGGA |
| 4551 | AGGCAAAATG | CCGCAAAAAA | GGGAATAAGG | GCGACACGGA | AATGTTGAAT |
| 4601 | ACTCATACTC | TTCCTTTTTC | AATATTATTG | AAGCATTTAT | CAGGGTTATT |
| 4651 | GTCTCATGAG | CGGATACATA | TTTGAATGTA | TTTAGAAAAA | TAAACAAATA |
| 4701 | GGGGTTCCGC | GCACATTTCC | CCGAAAAGTG | CCACCTGACG | TCTAAGAAAC |
| 4751 | CATTATTATC | ATGACATTAA | CCTATAAAA | TAGGCGTATC | ACGAGGCCCT |
| 4801 | TTCGTCTCGC | GCGTTTCGGT | GATGACGGTG | AAAACCTCTG | ACACATGCAG |

| 4851 | CTCCCGGAGA | CGGTCACAGC | TTGTCTGTAA | GCGGATGCCG | GGAGCAGACA |
|------|------------|------------|------------|------------|------------|
| 4901 | AGCCCGTCAG | GGCGCGTCAG | CGGGTGTTGG | CGGGTGTCGG | GGCTGGCTTA |
| 4951 | ACTATGCGGC | ATCAGAGCAG | ATTGTACTGA | GAGTGCACCA | TATGCGGTGT |
| 5001 | GAAATACCGC | ACAGATGCGT | AAGGAGAAAA | TACCGCATCA | GGCGAAATTG |
| 5051 | TAAACGTTAA | TATTTTGTTA | AAATTCGCGT | AAATATTTG  | TTAAATCAGC |
| 5101 | TCATTTTTTA | ACCAATAGGC | CGAAATCGGC | AAAATCCCTT | ATAAATCAAA |
| 5151 | AGAATAGACC | GAGATAGGGT | TGAGTGTTGT | TCCAGTTTGG | AACAAGAGTC |
| 5201 | CACTATTAAA | GAACGTGGAC | TCCAACGTCA | AAGGGCGAAA | AACCGTCTAT |
| 5251 | CAGGGCGATG | GCCCACTACG | TGAACCATCA | CCCAAATCAA | GTTTTTTGCG |
| 5301 | GTCGAGGTGC | CGTAAAGCTC | TAAATCGGAA | CCCTAAAGGG | AGCCCCCGAT |
| 5351 | TTAGAGCTTG | ACGGGGAAAG | CCGGCGAACG | TGGCGAGAAA | GGAAGGGAAG |
| 5401 | AAAGCGAAAG | GAGCGGGCGC | TAGGGCGCTG | GCAAGTGTAG | CGGTCACGCT |
| 5451 | GCGCGTAACC | ACCACACCCG | CCGCGCTTAA | TGCCGCCTA  | CAGGGCGCGT |
| 5501 | CCATTCGCCA | TTCAGGCTGC | GCAACTGTTG | GGAAGGGCGA | TCGGTGCGGG |
| 5551 | CCTCTTCGCT | ATTACGCCAG | CTGGCGAAAG | GGGGATGTGC | TGCAAGGCGA |
| 5601 | TTAAGTTGGG | TAACGCCAGG | GTTTTCCCAG | TCACGACGTT | GTAAAACGAC |
| 5651 | GGCCAGTGAA | TTGTAATACG | ACTCACTATA |            |            |

VECTOR FOR IN VITRO MUTAGENESIS AND USE THEREOF

RELATED APPLICATION

This is a continuation of application Ser. No. 474,630, filed Jan. 29, 1990, abandoned, which is a continuation-in-part of application Ser. No. 460,470, filed Jan. 3, 1990, abandoned.

FIELD OF THE INVENTION

The present invention pertains generally to the field of molecular biology and recombinant DNA technology. Specifically, the invention is directed to site-specific mutagenesis in a DNA sequence.

BACKGROUND OF THE INVENTION

Through the development of recombinant DNA techniques, it has become fairly straightforward to clone DNA sequences from essentially any organism into plasmid or viral vectors for propagation and amplification in a foreign host. In this form the DNA can be studied with regard to its sequence, structure, coding capacity or other properties. It can also be used for a variety of applications such as detection of complementary sequences in samples and the generation of altered forms of a gene product.

One method for producing altered forms of a gene is known as site-specific mutagenesis. Site-specific mutagenesis is a term used to denote the generation of specific base substitutions at selected sites in the DNA. Site-specific mutagenesis is a valuable tool for the study of DNA function and protein structure and function. A number of different mutagenesis methods have been reported (Smith, M., 1985, *Ann. Rev. Genet.* 19, 4233; and Section IV, Chapters 17–21, 1987, *Meth. Enzymol.*, 154, 329–414). Hutchison. et al. (1978, *J. Biol. Chem.*, 253, 6551–6560) introduced a method to obtain site-specific changes in DNA sequences using single-stranded DNA (ssDNA) and a synthetic oligonucleotide. The oligonucleotide is complementary to the single-stranded template DNA except for a region of mismatch in the center. It is this region that contains the desired nucleotide change or changes. According to Hutchison, et al., the general method for obtaining site-specific changes in a DNA sequence is as follows. The synthetic oligonucleotide is hybridized to the ssDNA. This mismatched hybrid (heteroduplex) serves as a template for the enzymatic synthesis of a complementary mismatch (mutant) strand. Following hybridization, the oligonucleotide is extended with DNA polymerase to create a double-stranded structure. The nick is then sealed, and the resulting heteroduplex is transformed into *Escherichia coli* (*E. coli*) host. Upon DNA replication and strand segregation, the cell contains a mixture of wild-type and mutant templates. Because mutant and wild-type plasmids are present in the same cell, a second round of transformation is generally employed to insure genetic purity. This method of in vitro mutagenesis is generally employed using single-stranded M13 or phagemid templates. Although the yield of mutants should theoretically be 50%, in practice the yield is much lower. Contributing factors, such as incomplete in vitro polymerization, primer displacement by a DNA polymerase used in the fill-in reaction and in vivo host-directed mismatch repair mechanisms, which favor repair of unmethylated newly synthesized DNA strands (Kramer, B. et al., 1984, *Cell*, 38, 879), contribute to the lower yield.

In order to increase the frequency with which the desired mutation is isolated, a number of selection techniques have been described. These selection techniques are generally directed to a method for constructing a mutation in DNA by hybridizing a section of parent DNA with a synthetic oligonucleotide which is mostly complementary to the parent DNA strand, but has one or more base pair mismatches at the desired point of mutation. This hybridized DNA strand is transformed into a bacterial host where the hybridized DNA strand can replicate, with the strand having the mismatch serving as the template for the desired mutation. The problem that exists at this point is that mutant and non-mutant strands of DNA are present and the mutant strand must be isolated.

Kramer, et al. (1984, *Nucleic Acids Res.* 12, 9441–9456) describe a method for introducing mutations into recombinant genomes of filamentous phage M13 ssDNA. The method involves the construction of a double-stranded "gapped duplex" DNA where the (+) longer strand parent DNA has two amber mutations which prevent it from replicating in a non-suppressing host. An "amber mutation" is a class of suppressible mutations that results in the creation of a UAG codon in mRNA. This codon normally signifies translation termination, so that polypeptide synthesis stops at the amber site. The shorter (−) DNA strand has the two amber mutations removed. When a mismatched synthetic oligonucleotide is hybridized to the single stranded DNA in the gap of the gapped duplex and connected with the rest of the (−) strand, the newly constructed (−) strand can replicate in a non-suppressing host. For this reason, the parent (+) strand with the amber mutations can be selected against the newly constructed (−) strand. Kramer, et al. report mutant recovery of 70 percent or more. A drawback of this system is that the complementary strand of the restriction fragment can compete with the ssDNA for hybridization, and the reannealed fragment can create a background of non-mutant plaques.

Another selection strategy is based on the method of Kunkel (1985, *Proc. Natl. Acad. Sci.* 82, 488–492) and Kunkel, et al. (1987 *Methods Enzymol.* 154, 367–382). In this scheme ssDNA is prepared in a special *E. coli* host which is $dut^-ung^-$. This phenotype results in the occasional substitution of uracil for thymidine in the DNA strand. Mutagenesis is performed in the usual manner by hybridizing a mismatched oligonucleotide to the ssDNA template and filling in the outside strand with DNA polymerase. When this molecule is transformed into a $dut^+ung^+$ *E. coli* strain, the inside strand containing the uracil substitutions is cleaved and destroyed, leaving only the mutant strand intact. However, a low number of transformants is generally obtained.

Variations of the in vitro mutagenesis technique using two oligonucleotide primers have also been described (Zoller, M. J. and Smith, M. *Methods in Enzymology* (1987) Vol. 154, 329–351) and have been used without either of the oligonucleotides conferring a selectable phenotype (Norris, et al. 1983, *Nucleic Acids Res.* 11, 5103–5113).

Carter, et al. (1985, *Nucleic Acids Res.* 13, 4431–4443) describe a method for the construction of mutations in M-13 vectors using synthetic oligonucleotides whereby the DNA is first cloned into an engineered M13 vector which carries a genetic marker so that it can be selected against the parent strand. The technique used is referred to as "coupled priming" where one oligonucleotide with base-pair mismatches is hybridized to the parent DNA strand to construct the mutation of interest, and a second oligonucleotide which contains a selectable marker, is also hybridized to the parent strand. The two oligonucleotides are connected to make a continuous strand of DNA. This heteroduplex DNA is transfected into a mismatch repair deficient strain of E. coli which can select against the parent strand. In this case the primary marker used is an EcoK or EcoB marker which will cause the strand to be cleaved if transfected into an organism with that restriction enzyme. For example, by transfecting into a host organism that has the EcoK restriction enzyme, one can select against a parent strand containing an EcoK site, which will be cleaved. Because the EcoK marker can be changed to an EcoB marker by changing just one base pair, it is possible to cycle between the two markers for successive rounds of mutation by simply hybridizing a marker strand with the one base pair change to the parent strand. Mutant yields of up to 70 percent were reported with this process. However, it is unlikely that this method will work if the section of DNA cloned into the M13 vector contains an EcoK or EcoB site, since that site would also be cleaved.

Stanssens et al. (1989, Nucleic Acids Res. 17, 4441–4454) are directed to a method of construction of multiple mutations in a sequential manner through oligonucleotide-directed mutagenesis. Unlike Kramer, et al. and Carter, et al., Stanssens, et al. construct mutations in plasmids, which are doubled-stranded rather than in M-13 phage vectors, which are single-stranded. The Stanssens, et al. method utilizes the Kramer, et al. method of mutation insertion into a gapped-duplex DNA. In order to construct the gapped-duplex DNA, it is necessary to take double-strand plasmid DNA and turn it into ssDNA. This is accomplished because the plasmid used has had the origin of replication for the filamentous phage f1 (f1 replication origin) engineered into it, and this can be used to generate ssDNA. The orientation of the f1 DNA determines which of the two strands of the plasmid will be secreted. This allows one directional copying of one strand of the plasmid DNA. The chimeric ssDNA phage-plasmid vector containing a phage replication origin is known as a "phagemid."

In the Stanssens, et al. method, the gapped-duplex DNA is constructed using two complementary plasmids. One contains an ampicillin resistance gene and a chloramphenicol resistance gene that has been inactivated with an amber mutation, making the plasmid chloramphenicol sensitive; and a second plasmid that is chloramphenicol resistant and has an ampicillin resistance gene inactivated with an amber mutation. Antibiotic resistance is used to select for the mutant strands of DNA. Because the two plasmids have opposite antibiotic resistances, by alternating construction of the gapped duplex, additional mutations can be inserted in successive rounds of mutation and one may alternately select for the mutant strand. Both plasmid vectors contain a multilinker region which provides an area for insertion of target sequences for mutagenesis. One disadvantage of this technique is that hybridization of the antibiotic resistance restoration strand is inefficient because of its source as a double-stranded restriction fragment, the other strand which competes with the ssDNA for hybridization. In addition, reformed double-stranded restriction fragments will create a background of ampicillin resistant non-mutant colonies, limiting the efficiency of the method.

Two other methods have been described for the selection of the mutant strand following the fill-in reaction in oligonucleotide directed in vitro mutagenesis. Vandevar, et al. (1988, Gene 65, 129–133) performed the fill-in reaction using 5-methyl dCTP to form a hemimethylated duplex strand. Nicks are introduced selectively into the nonmethylated parent strand through the action of the restriction endonuclease Msp I. The parent strand is then degraded through the action of exonuclease III. In a similar system sold by Amersham Corp., the in vitro fill-in reaction following hybridization of a mismatched oligonucleotide to a ssDNA template is performed using alpha-thio dCTP. The non-phosphorothioate non-mutant strand is then nicked specifically with the restriction enzyme Nci I and then degraded by the action of exonuclease III. Mutagenesis efficiencies of up to 95% are reported in this system. However, a drawback is the relatively large amount of DNA needed (up to 20 micrograms (ug)) to perform a reaction and transformation. Further, the system requires a series of complex enzymatic reactions.

SUMMARY OF THE INVENTION

In accordance with the present invention, it is possible to obtain site-specific in vitro mutagenesis and selection for the mutation using a plasmid which does not normally confer resistance on its host. The in vitro mutagenesis system consists of a unique mutagenesis vector and a straightforward procedure for selection of oligonucleotide-directed mutants.

The present invention is generally directed to a method for obtaining site-specific in vitro mutagenesis in a DNA sequence comprising providing a double-stranded DNA molecule vector containing an inactivated first genetic marker which first genetic marker is capable of being restored to functional expression, an active second genetic marker, a polylinker region and an f1 replication origin. A ssDNA template is formed from the DNA molecule vector. At least one mismatched mutagenic oligonucleotide and a restoration oligonucleotide is hybridized to the ssDNA template to form a heteroduplex. The restoration oligonucleotide is capable of activating the expression of the first genetic marker. The heteroduplex is then converted to a full-length dsDNA molecule, and the dsDNA molecule is transformed into an E. coli, which is plated under selective conditions which only allow survival and growth of the host if it expresses a functional first genetic marker.

The genetic markers are preferably antibiotic resistance markers. For example, the first genetic marker can be an ampicillin resistance gene, and the second genetic marker can be a tetracycline resistance gene.

In this regard, the invention is also directed to a method for obtaining site-specific in vitro mutagenesis in a DNA sequence comprising providing a DNA cloning vector containing an inactivated first antibiotic resistance gene wherein the inactivated antibiotic resistance gene may be reactivated to antibiotic resistance. The vector also includes a second antibiotic resistance gene in active form, wherein the second antibiotic resistance gene has been modified to remove sites for the restriction enzymes Hind III, Bam H1, Sph I and Sal I. The vector also includes a polylinker region and an f1 replication origin.

An ssDNA template is formed from the DNA molecule vector. At least one mismatched mutagenic oligonucleotide and an antibiotic restoration oligonucleotide is hybridized to form a heteroduplex, wherein the antibiotic restoration oligonucleotide is capable of activating the expression of antibiotic resistance to the first antibiotic resistance gene. The heteroduplex is converted to a full-length dsDNA molecule by adding the deoxynucleotides deoxyadenosine 5'-triphosphate (dATP) deoxycytosine 5'-triphosphate (dCTP) deoxyguanosine 5'-triphosphate (dGTP) and deoxythymidine 5'-triphosphate (dTTP) in the presence of T4 DNA polymerase and T4 DNA ligase. The dsDNA molecule is then transformed into a repair minus E. coli host. The double-strand molecule is then grown in a host in the presence of an antibiotic to the first antibiotic resistance gene to identify the resistant colonies performed by this process. The antibiotic resistant colonies are then screened for the presence of the mutation.

The present invention is also directed to a DNA vector for use in the production of site-specific mutagenesis comprising a double-stranded DNA molecule having an inactivated first genetic marker which first genetic marker is capable of being restored to functional expression. The DNA vector also includes an active second genetic marker, a polylinker region and an f1 replication origin. Examples of the genetic markers are described above.

The present invention is further directed to a DNA vector for use in production of site-specific mutagenesis comprising a double-stranded DNA molecule having an inactive ampicillin resistance gene from the plasmid pBR322 which gene is capable of reactivation. The ampicillin resistance gene has been modified by removing the Pst I site, resulting in a frame-shift mutation and consequent inactivation. The vector also includes a tetracycline resistance gene from the plasmid pBR322 wherein the tetracycline resistance gene has been modified to remove sites for the restriction enzymes Hind III, Bam H1, Sph I and Sal I. Finally, the vector contains a polylinker region from the plasmid pGEM®-3Zf(+), and an f1 replication origin from the plasmid pGEM®-3Zf(+).

The present invention is further directed to a plasmid for use in the production of site-directed mutagenesis in a DNA sequence comprising an essentially pure plasmid in substantially circular form having an inactivated ampicillin resistance gene which gene is capable of being reverted to the expression of ampicillin resistance, a tetracycline resistance gene, a polylinker region and an f1 replication origin region.

The present invention is further directed to a kit for conducting site-specific in vitro mutagenesis in a DNA sequence comprising a container containing double-stranded DNA plasmid vectors having an inactivated first genetic marker which is capable of being restored to functional expression, a second active genetic marker, a polylinker region and an f1 replication origin; a container containing helper phages to produce single-stranded DNA from the double-stranded DNA plasmid vectors, a container containing an oligonucleotide capable of restoring functional expression to the inactivated first genetic marker, and a container containing an E. coli host.

The site-specific in vitro mutagenesis technique of the present invention has a variety of applications, including, but not limited to, the study of critical amino acid residues involved in enzymatic activity, the study of DNA promoter and enhancer function and structure, the study of residues important in protein folding, the study of residues involved in subunit-subunit interactions, the study of the structure of DNA binding sites for proteins, the study of functions of particular residues or domains in protein stability, the creation of mutant proteins with increased stability or resistance to environmental agents, and the study of effects of removing sites for protein modification, such as phosphorylation or glycosylation.

The site-specific in vitro mutagenesis method of the present invention has several advantages over the prior art. For example, the use of the method of the present invention, known as "coupled priming," rather than the prior art gapped-duplex method, is superior in that it is simpler to perform. Further, the present invention requires only one plasmid with an inactivated genetic marker which marker can be reactivated for selection of mutant strands. Additionally, only a short segment of an oligonucleotide is needed to correct the frame-shift mutation in the inactivated gene marker and restore the gene to its active form. Further, by using only ssDNA, the competition for hybridization at the site of mutation is reduced.

The present invention can be expanded to couple two mutagenic oligonucleotides with the restoration oligonucleotide and obtain good linkage of all three oligonucleotides. Thus, it is possible to insert two or more mutations in one round of mutagenesis.

Further objects, features and advantages of the invention will be apparent from the following detailed description of the invention and the illustrative drawings.

BRIEF DESCRIPTION OF THE DRAWINGS

In the drawings:

FIG. 2 illustrates the plasmid promoter and multiple cloning site sequence of the plasmid pSELECT-1

FIG. 3 depicts the restriction sites for the plasmid vector pSELECT-1

FIG. 4 depicts the DNA sequences of the plasmid vector pSELECT-1

DETAILED DESCRIPTION OF THE INVENTION

Figure 1:
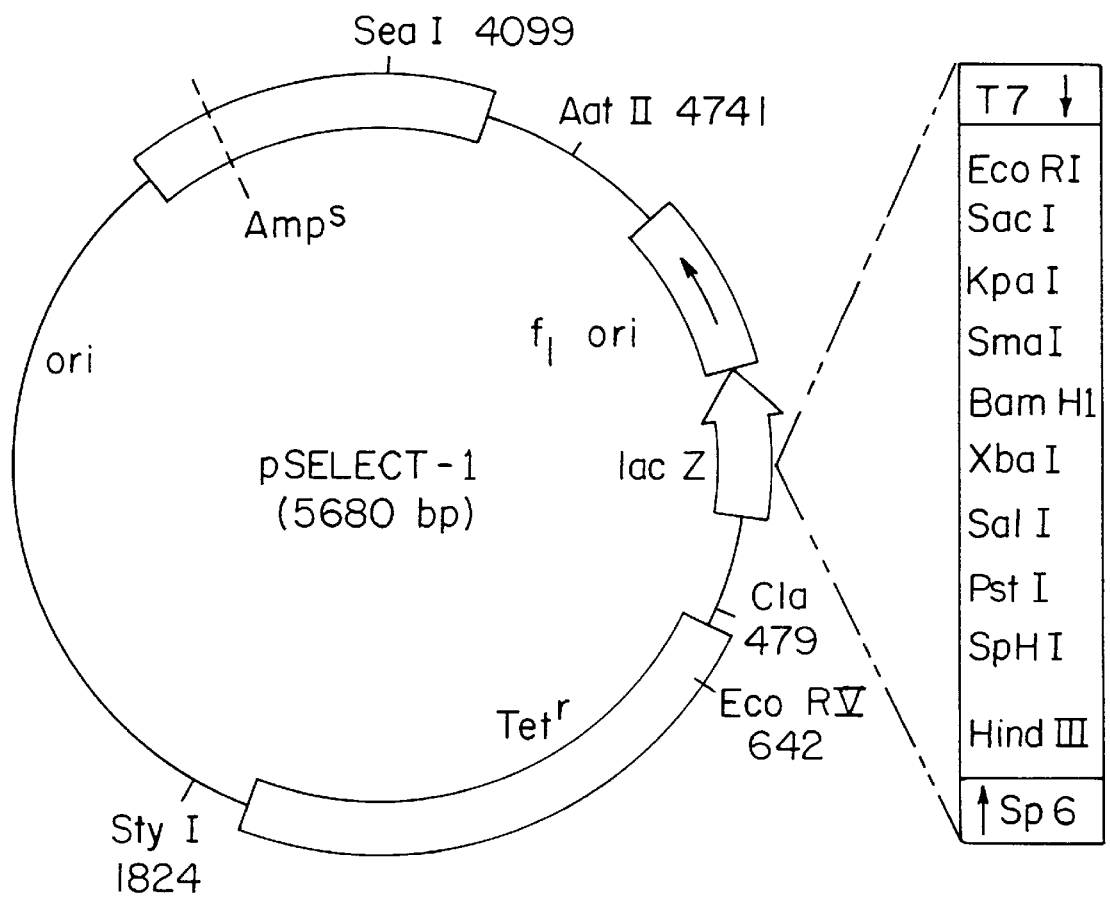
FIG. 1 is a partial restriction site and functional map of the plasmid pSELECT-1

The present invention is directed to a site-specific mutagenesis procedure in a DNA sequence utilizing a specially engineered plasmid vector. The process is based on the use of a second mutagenic oligonucleotide to confer resistance to the mutant DNA strand.

For purposes of the present invention, the term "genetic marker" or "marker" is intended to mean a gene conferring a specific characteristic, such as resistance to an antibiotic, which can be recognized and used to select cells. For example, if the gene conferring resistance to the antibiotic tetracycline is inserted into a host bacterium using a suitable plasmid vector and the complete culture is plated out on agar medium containing tetracycline, only the cells with the marker gene will survive.

The Vector

The vector for use in the in vitro mutagenesis method carries two selectable genetic markers, one of which is inactivated but which can be restored via a restoration of function mutation using a specific oligonucleotide. There are two basic requirements for the genetic markers of the vector of the present invention: 1) one marker is needed to propagate the plasmid; and 2) another marker undergoes a restoration of function mutation, which will be described hereinafter.

The vector of choice in the present invention is termed a pSELECT-type vector (Promega Corporation), which includes an ampicillin resistance gene. A crucial feature of the pSELECT plasmid vector is that the ampicillin resistance gene is modified by removing the Pst-I site from the gene. This results in a four-base pair frameshift and the inactivation of the ampicillin resistance gene. The ampicillin resistance gene is restorable to functionality, i.e., is capable of being reverted to the expression of ampicillin resistance, by an ampicillin restoration oligonucleotide primer, which is extended in vitro using T4DNA polymerase to reconstruct the correct, i.e., active, gene. The linking of the oligonucleotide restoring antibiotic resistance to the mutagenic oligonucleotide creates a simple method for selecting for the mutant strand.

Another feature of the pSELECT vector is the incorporation of a second antibiotic resistance gene, for example a tetracycline resistance gene, from plasmid pBR322. The tetracycline resistance gene specifies tetracycline resistance and is necessary in order to grow the vector before ampicillin resistance has been reverted. The tetracycline resistance gene is necessarily modified to remove particular restriction sites in order to make these sites unique elsewhere, i.e., in the polylinker region, within the vector. The tetracycline resistance gene is modified by removing the following enzyme restriction sites while keeping the amino acid sequence of the encoded protein unchanged and retaining tetracycline resistance: Hind III, Bam H1, Sph I and Sal I sites.

The pSELECT plasmid vector also contains the polylinker region and the f1 replication origin from the plasmid pGEM®3Zf(+). The polylinker region provides the area of insertion of target sequences for mutagenesis. The f1 replication origin allows one to make ssDNA containing the tetracycline resistance gene to serve as a template to modify target sequence by in vitro mutagenesis.

pSELECT-1 Vector

The preferred vector for the in vitro mutagenesis system described herein is a plasmid vector named pSELECT-1. Reference is made to FIG. 1 which illustrates a partial restriction site and functional plasmid circle map of pSELECT-1. FIG. 2 illustrates the promoter and multiple cloning site sequence of the plasmid pSELECT-1. A table of the restriction sites and a table of the DNA sequence for the plasmid pSELECT-1 are illustrated on FIGS. 3 and 4, respectively.

The pSELECT-1plasmid is a phagemid, defined as a chimeric plasmid containing the origin of replication of a ssDNA bacteriophage. This phagemid produces ssDNA upon infection of the host cells with the helper phage R408 or M13K07 (Dotto, G. P. et al., 1981, *Virology*, 114, 463; Dotto, G. P. et al., 1984, *J. Mol. Biol.*, 172, 507). The vector contains a multiple cloning site (polylinker region) flanked by the SP6 and T7 RNA polymerase promoters and inserted into the lacZ alpha-peptide gene. Cloning of a DNA insert into the mcs results in inactivation of the alpha-peptide gene. When plated on indicator plates, colonies containing recombinant plasmids are white in a background of blue colonies. The SP6 and T7 promoters may be used to generate high specific activity RNA probes from either strand of the insert DNA. These sites also serve as convenient priming sites for sequencing of the insert. The pSELECT-1 vector carries gene sequences for both ampicillin and tetracycline resistance. However, the plasmid is ampicillin sensitive because a frameshift was introduced into this resistance gene by cutting with Pst I, blunting the ends with Klenow and religating. Therefore, propagation of the plasmid and recombinants is performed using tetracycline selection. The phagemid vector pSELECT-1 has 5680 base pairs and is characterized by the following sequence reference points:

| | |
|---|---|
| a. T7 RNA polymerase transcription initiation site | 1 |
| b. SP6 RNA polymerase transcription initiation site | 69 |
| c. T7 RNA polymerase promoter | 5654–5680 |
| d. SP6 RNA polymerase | 70–86 |
| e. multiple cloning sites | 5–61 |
| f. lacZ start codon | 108 |
| g. lac operon sequences | 5501–5661 |
| h. lac operator | 128–144 |
| i. beta-lactamase coding region | 3750–4606 |
| j. phage f1 origin of replication | 5045–5500 |
| k. binding site of pUC/M13 forward sequencing primer | 5621–5637 |
| l. binding site of pUC/M13 reverse sequencing primer | 104–120 |

Figure 5:
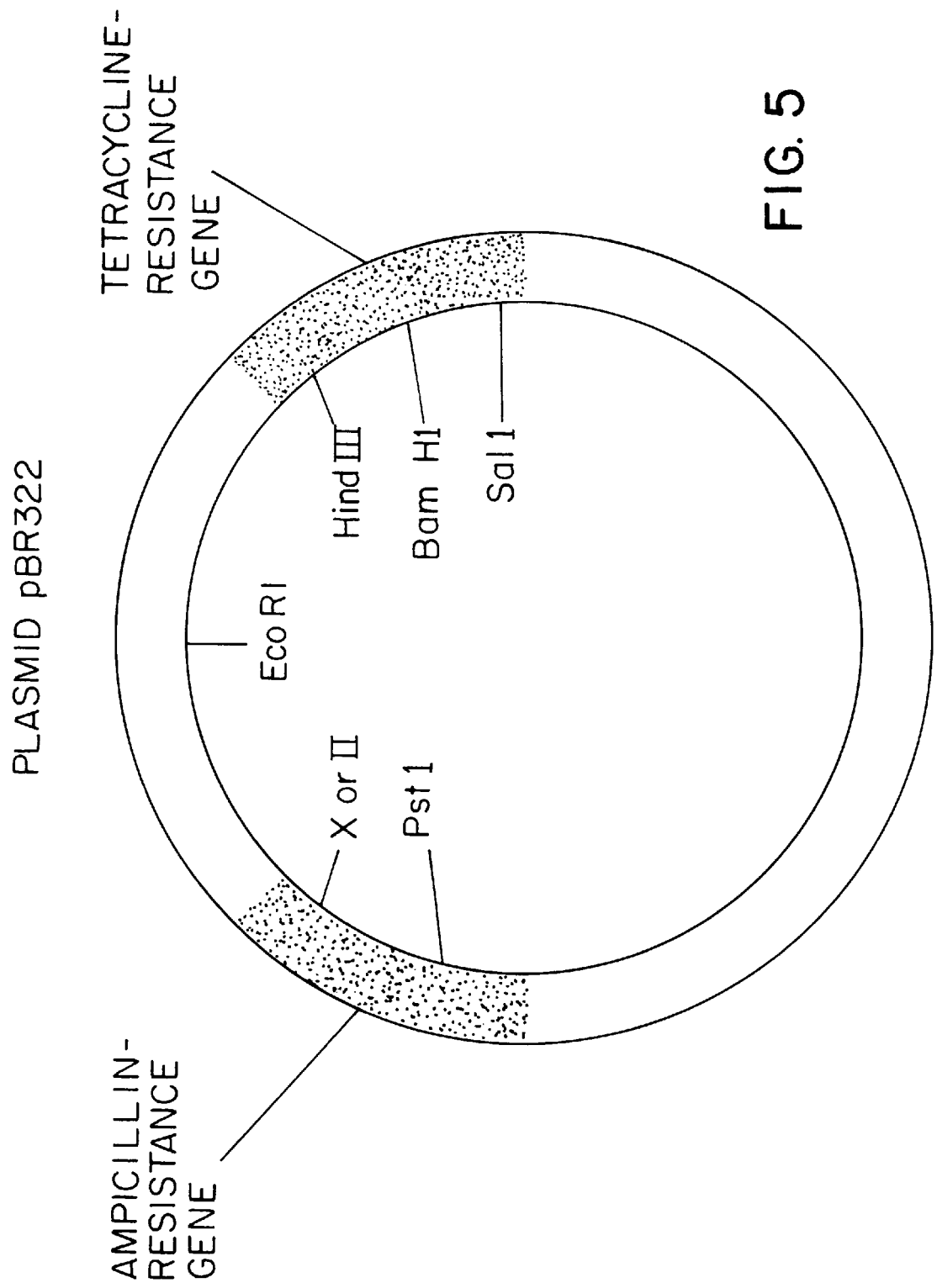
FIG. 5 is a partial restriction site and functional map of the plasmid pBR322.
Figure 6:
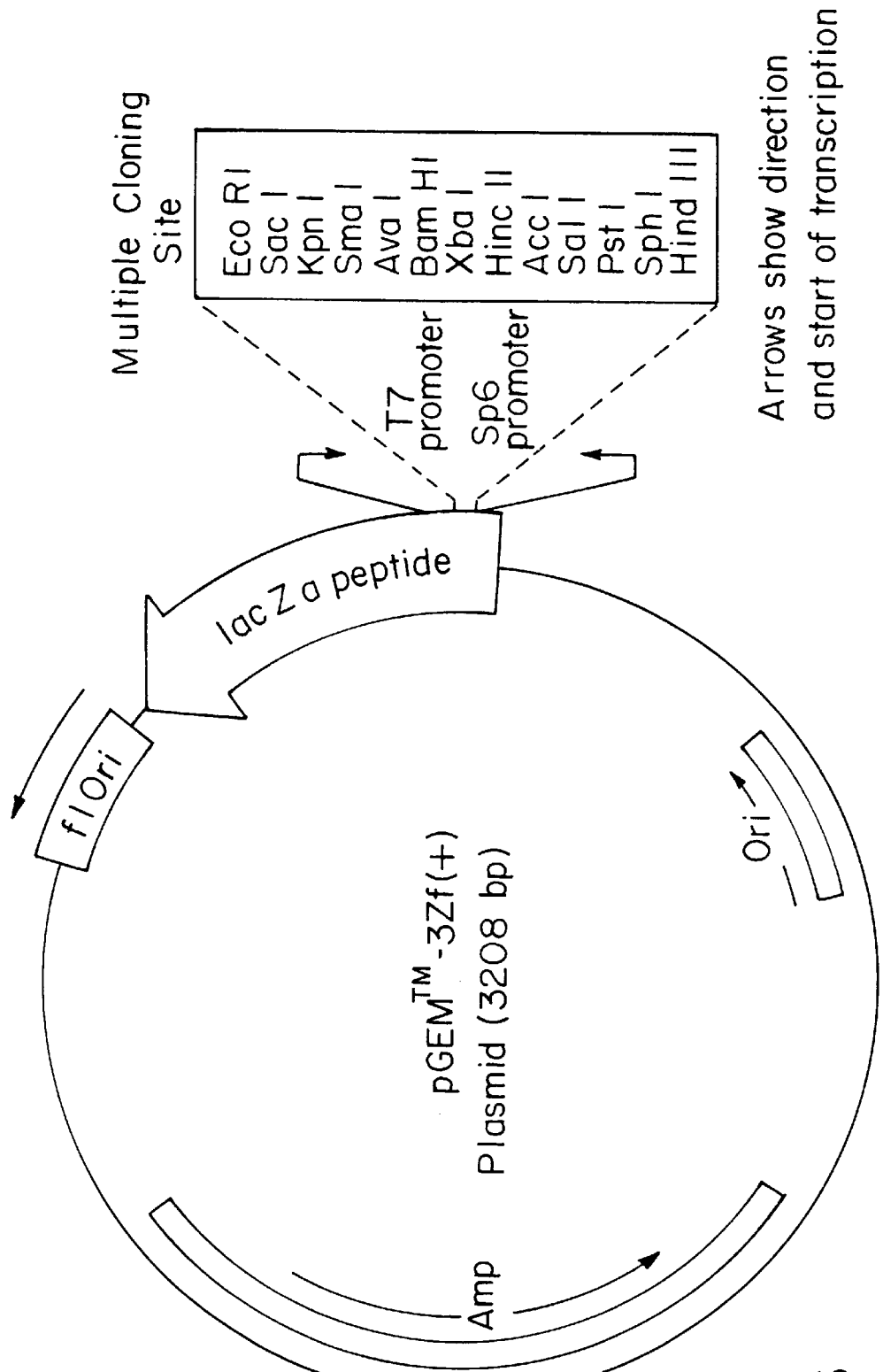
FIG. 6 is a partial restriction site and functional map of the plasmid pGEM®-3Zf(+).

The phagemid pSELECT-1 is engineered to have the ampicillin and tetracycline resistance genes from the plasmid pBR322, illustrated in FIG. 5, and the polylinker region and the f1 replication origin from the plasmid pGEM®-3Zf (+), illustrated in FIG. 6. Essentially, large restriction fragments of the plasmids are reconnected to form a large circle. A more detailed explanation of the formation of pSELECT-1 phagemid is found in the examples.

A viable sample of the phagemid vector pSELECT-1 was deposited with the American Type Culture Collection (ATCC) on Dec. 21, 1989, having received ATCC Accession No.: 68196. Upon issuance of a patent on this application, all restrictions on the availability of the deposited material to the public will be irrevocably removed.

Other Vectors

Markers other than antibiotic resistance genes can be employed for purposes of the present invention. For example Carter, et al. (supra) uses two oligonucleotides and selects for the mutant strand by selecting against the parent strand. However this method does not utilize a selectable marker which undergoes a restoration of function mutation. Selection is achieved by creating a loss of function of a selectable marker, which results in the destruction of a restriction enzyme site in the mutant strand while leaving that site within the parental strand.

Nutritional markers can also be used along with antibiotic resistance markers. The antibiotic resistance marker can be used for the propagation of the plasmid and a nutritional marker can be inactivated and then restored to functionality using an oligonucleotide which is linked to a second mutagenic oligonucleotide. For this purpose, a strain would have to be used which, under defined conditions, was dependent on the particular nutritional factor for growth. One example of such a marker is a marker for leucine biosynthesis.

Another example of such a marker includes *E. coli* that is beta-galactosidase minus and cannot grow on lactose except in the presence of a plasmid carrying a functional beta galactosidase gene. The beta galactosidase gene on the plasmid could be inactivated and an oligonucleotide used to restore the function of this gene while coupling this oligonucleotide to a second mutagenic oligonucleotide. If linkage between the two oligonucleotides was achieved then the only colonies which would form on plates containing lactose would carry the desired mutation.

Another example involves a plasmid carrying the trpE gene on a plasmid as a selection for transformed trpE minus bacteria. An example of such a plasmid is pRK353 which carries trpE (Dean, D., 1981, *Gene* 14, 99–102). The trpE marker on the plasmid could be rendered inactive in a fashion that was restorable using ssDNA and an oligonucleotide. The trpE restoring oligonucleotide could be linked to a second mutagenic oligonucleotide providing a selection for mutation.

Another type of marker could utilize a color test for mutation. The marker chosen for the restoration of function mutation in this situation need not be strictly a selectable marker, but also one which can be screened for. An example of a suitable color test marker is known as a pSELECT-Control vector. The pSELECT-Control vector provides a convenient white/blue positive control for mutagenesis reactions. This vector is derived from pSELECT-1 by cutting the Pst I site within the polylinker, blunting the ends with Klenow fragment and religating. This introduces a frameshift into the lacZ gene, resulting in a white colony phenotype on indicator plates. A lacZ repair oligonucleotide is used to introduce a four-base insertion which corrects the defect in the lacZ gene and restores colony color to blue. The efficiency of the system in selecting for this repair mutation can be checked by the user; the fraction of blue colonies obtained gives the mutagenesis frequency. When the lacZ repair oligonucleotide is used in combination with the ampicillin repair oligonucleotide to correct this defect, 80–90% of the ampicillin resistant colonies should be blue. When the lacZ repair oligonucleotide is used alone, a mutagenesis frequency of only about 2–5% is seen.

Uses and Application

Figure 7:
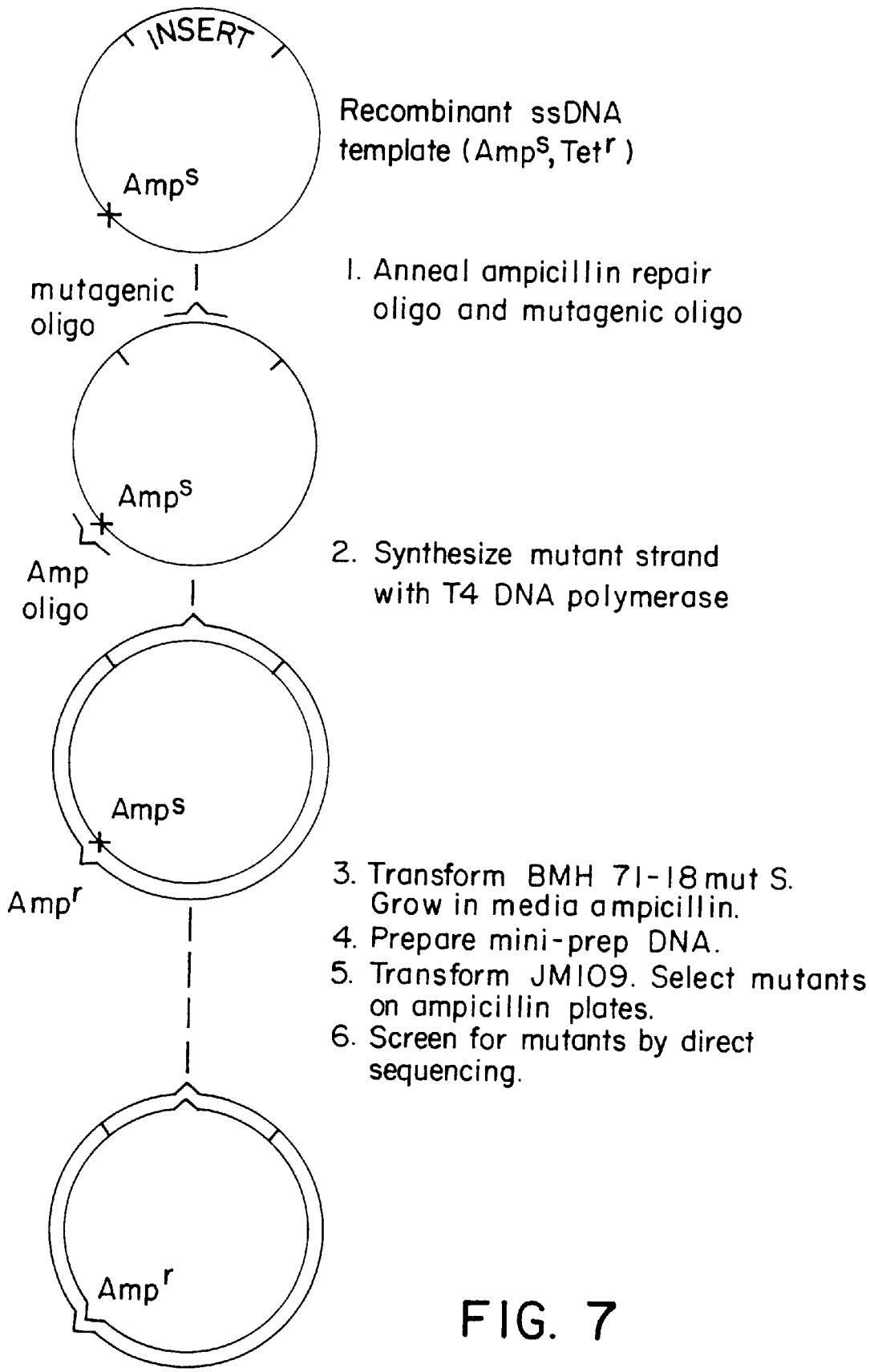
FIG. 7 is a schematic diagram of a preferred embodiment of an in vitro mutagenesis system of the present invention.

As noted previously, the vector described above has a variety of uses and applications. One such application is for site-specific in vitro mutagenesis in a DNA sequence. While it is within the scope of the present invention to utilize any vector conforming to the above description, the example of site-specific in vitro mutagenesis will be described with respect to the pSELECT-1 vector. Reference is now made to FIG. 7 for a schematic diagram of the in vitro mutagenesis system described in the following paragraphs.

In this method ssDNA is prepared from the pSELECT-1 vector according to methods known to the art. Reference is made to the *pGEM® Single-strand System Technical Manual* (June 1987, Promega Corp.), which is incorporated herein by reference for a detailed description of a method for preparing a ssDNA template from a plasmid vector.

In the second step, a mismatched mutagenic oligonucleotide and an ampicillin restoration oligonucleotide, as described previously, are hybridized to the ssDNA template. The mutagenic oligonucleotide must be complementary to the single-strand target DNA. The ssDNA produced by the pSELECT-1 phagemid is complementary to the lacZ coding strand. The stability of the complex between the oligonucleotide and the target strand is determined by the base composition of the oligonucleotide and the conditions under which it is annealed. In general a 17–20 base pair (bp) oligonucleotide with the mismatch located in the center will be sufficient for single bp mutations. This gives 8–10 perfectly matched nucleotides on either side of the mismatch. For mutations involving two or more mismatches, oligonucleotides 25 bp or longer are needed to allow for 12–15 perfectly matched nucleotides on either side of the mismatch. Oligonucleotides 26 and 27 bp long can be used successfully to perform four base insertions and deletions. A significant increase in the number of mutants is observed when oligonucleotides are phosphorylated, presumably due to increased linkage between the ampicillin repair oligonucleotide and mutagenic oligonucleotide. Therefore, the oligonucleotides are 5'-phosphorylated.

The ampicillin restoration oligonucleotide is physically linked to the mutagenic oligonucleotide via an 30 extension or fill-in reaction. The annealing conditions required may vary with the base composition of the oligonucleotide. Adenosine (A)/Thymine (T) complexes tend to be less stable than Guanosine (G)/Cytosine (C)-rich complexes and may require a lower annealing temperature to be stabilized. Routinely, oligonucleotides can be annealed by heating to 70° C. for 5 minutes followed by slow cooling to room temperature. The ampicillin restoration oligonucleotide is capable of restoring the expression of ampicillin resistance to the inactivated ampicillin resistance gene from the pSELECT-1 vector.

The heteroduplex formed by the hybridization of the mismatched mutagenic oligonucleotide and the ampicillin restoration oligonucleotide primer is then converted to a full-length double-strand DNA molecule by filling the gaps between the primers using deoxynucleotides and T4 DNA polymerase, according to the method described in Sambrook, et al. (1989, *Molecular Cloning-A Laboratory Manual*, 2nd edition, Cold Spring Harbor Laboratory Press, Chapter 15), which is incorporated herein by reference. The resulting nicks are then sealed with T4 DNA ligase.

The resultant DNA sequence is then transformed into a repair minus strain of *E. coli*. A preferred example of a repair minus *E. coli* host is BMH 71-18 mut S (Kramer, et al., 1984, supra; and Zell and Fritz, 1987, *Embo S.* 6,1809), which is a highly transformable mismatch repair minus strain of *E. coli*. Use of this strain prevents in vivo repair of the newly synthesized unmethylated strand, leading to high mutation efficiencies. BMH 71-18 mut S is recA+ and, as a result, inserts containing highly repetitive sequences may be unstable. The strain is then grown in the presence of ampicillin.

The plasmid DNA from the resulting ampicillin resistant colonies is then isolated from this culture and again used to transform *E. coli*. An example of a preferred *E. coli* host for this second round of transformation reaction is JM109 (Kramer, et al., 1984, supra). JM109 is a useful host in which to clone pSELECT and pGEM® vectors and for the production of single-stranded DNA from M13 or phagemid vectors (Masamune and Richardson, 1971, *J. Biol. Chem.* 246, 2692). The strain grows well and is efficiently transformed by a variety of methods. Because JM109 is recA– and lacks the *E. coli* K restriction system, undesirable restriction of cloned DNA and recombination with host chromosomal DNA are prevented. The endonuclease A1 mutation leads to an improved yield and quality of isolated plasmid DNA. Thus, JM109 or a similar host ensures proper segregation of mutant and wild-type plasmids and results in a high proportion of mutant colonies.

These resultant ampicillin resistant colonies are picked and examined for the presence of mutation. It is within the scope of this invention to utilize any examination techniques known to the art. A preferred examination technique is the DNA sequencing described in Sambrook, et al., 1989, supra, at Chapter 13 ("DNA sequencing").

An additional method, known as blue/white color screening is particularly adaptable to the *E. coli* host described above. The JM109 and BMH71-18 mut S strains can be used for blue/white color screening of pSELECT-1 and pSELECT-control vectors. These strains are deficient in beta-galactosidase activity due to deletions in both genomic and episomal copies of the lacZ gene. The deletion in the episomal (F-factor) copy of the lacZ gene (lacZ[delta]M15) is located in the alpha-peptide region and, as a result, beta-galactosidase activity can be complemented by addition of a functional alpha-peptide. The pSELECT vectors encode the lacZ alpha-peptide, and cells carrying these plasmids are able to produce functional beta galactosidase.

When plated on indicator media containing X-Gal (5-Bromo-4-Chloro-3 Indolyl beta-D-Galactopyranoside) and IPTG (Isopropyl beta-D-Thiogalactoside), the host/plasmid combination will generate blue colonies. However, when the alpha peptide is disrupted by cloning into the multiple cloning region for the pSELECT vector, complementation does not occur and no beta galactosidase activity is produced. Therefore, bacterial colonies harboring recombinant vector constructs remain white.

JM109 and BMH 71-18 mut S should always be maintained on minimal plates (M-9) supplemented with 1 mM thiamine-HCl. This selects for the presence of F' which carries a nutritional requirement for growth (proline biosynthesis) and decreases the number of false positives.

Kit

The present invention is also directed to a kit for conducting site-specific in vitro mutagenesis in a DNA sequence. The necessary components of the kit are as follows:

a) a container containing dsDNA molecule vectors having an inactivated genetic marker which is capable of being restored to functional expression, a second active genetic marker, a polylinker region and an f1 replication origin;

b) a container containing helper phages to produce ssDNA from the dsDNA molecule vectors;

c) a container containing an oligonucleotide capable of restoring functional expression to the inactivated genetic marker; and d) a container containing an E. coli host.

The dsDNA molecule vector is preferably pSELECT-1 and the oligonucleotide is preferably an ampicillin restoration oligonucleotide.

A preferred kit for conducting a site-specific in vitro mutagenesis according to the present invention follows. The quantity of the reagents are sufficient to perform 25 mutagenesis reactions:

| Quantity | Component |
| --- | --- |
| 20 ug | pSELECT-1 Phagemid Mutagenesis Vector |
| 20 ug | pSELECT-Control Vector (lacZ) |
| 30 ul | Ampicillin Repair Oligonucleotide |
| 30 ul | Control lacZ Repair Oligonucleotide |
| 75 ul | 10X Annealing Buffer |
| 100 ul | 10X Synthesis Buffer |
| 500 u | T4 DNA Polymerase |
| 100 u | T4 DNA Ligase |
| 0.5 ml | E. coli Strain BMH 71-18 mut S |
| 0.5 ml | E. coli Strain JM109 |
| 1.0 ml | Helper Phage R408 |
| 1.0 ml | Helper Phage M13K07 |

DESCRIPTION OF PREFERRED EMBODIMENT

A preferred method for conducting the process of the present invention will now be explained utilizing the pSELECT™ phagemid DNA vector. Cloning into the pSELECT™ Vector The DNA to be mutated can be cloned into the pSELECT™ vector using the multiple cloning site or polylinker site illustrated in FIGS. 1 and 2. The vector DNA is then transformed into competent cells of strain JM109 or a similar host and recombinant colonies are selected by plating on Luria-Bertani (LB) plates containing 15 ug/ml tetracycline, 0.5 mM IPTG, and 40 ug/ml X-Gal. LB medium consists of the following: 10 g of Bacto-Tryptone, 5 g of Bacto-Yeast extract, and 5 g NaCl. The pH is adjusted to 7.5 with NaOH and the medium is autoclaved.

After incubation for 24 hours at 37° C., colonies containing recombinant plasmids will appear white in a background of blue colonies. An alternative to preparing plates containing X-Gal and IPTG is to spread LB plates with 50 ul of 50 mg/ml X-Gal and 100 ul of 100 mM IPTG and allow these components to absorb for 30 minutes at 37° C. prior to plating cells.

Preparation of Phagemid Single-Strand DNA

To produce single-stranded templates for the mutagenesis reaction, individual colonies containing pSELECT™-Control or recombinant pSELECT-1™ phagemids are grown and the cultures are infected with helper phage as described below. The ssDNA produced is complementary to the lacZ coding strand and is also complementary to the strand of the multiple cloning site illustrated in FIG. 2.

Two helper phages R408 and M13K07 may optimize ssDNA yields. Differences in the yields and absolute amounts of plasmid and phage ssDNA have been observed to be dependent on the particular combination of host, vector and helper phage.

The following is a list of reagents to be supplied by the user:

7.5 m Ammonium acetate, pH 7.5

TYP broth

Phage precipitation solution

TE buffer

Chloroform: Isoamyl alcohol (24:1)

TE-saturated phenol/chloroform

Ethanol (100% and 70%)

The protocol for preparing phagemid single-stranded DNA is as follows:

1. Prepare an overnight culture of cells containing pSELECT1™ or pSELECT™-Control phagemid DNA by picking individual tetracycline resistant colonies from a fresh plate. Inoculate 1–2 ml of TYP broth containing 15 ug/ml tetracycline and shake at 37° C. A liter of TYP broth is prepared from the following: 16 g Bacto-tryptone, 16 g Bacto-yeast extract, 5 g NaCl, and 2.5 g $K_2HPO_4$. The mixture is autoclaved and cooled. Where indicated, ampicillin may be added to 100 ug/ml.

2. The next morning, inoculate 5 ml of TYP broth containing 15 ug/ml tetracycline with 100 ul of the overnight culture. Shake vigorously at 38° C. for 30 minutes in a 50 ml tube.

3. Infect the culture with helper phage R408 or M13K07 at an m.o.i. (multiplicity of infection) of 10, i.e., add 10 helper phage particles per cell. For the helper phages supplied with this system, add 40 ul. Continue shaking for 6 hours to overnight with vigorous agitation.

4. Harvest the culture supernatant by pelleting the cells at 12,000×g for 15 minutes. Pour the supernatant into a fresh tube and spin again for 15 minutes.

5. Precipitate the phage by adding 0.25 volume of phage precipitation solution (pg.) to the supernatant. Leave on ice for 30 minutes, then centrifuge for 15 minutes at 12,000×g. Thoroughly drain the supernatant.

6. Resuspend the pellet in 400 microliters/ul of TE buffer (pg.) and transfer the sample to a microcentrifuge tube.

7. Add 0.4 ml of chloroform: isoamyl alcohol (24:1) to lyse the phage, vortex for 1 full minute, and centrifuge in a microcentrifuge (12,000×g) for 5 minutes. This steps removes excess polyethylene glycol (PEG).

8. Transfer the upper, aqueous phase (containing phagemid DNA) to a fresh tube, leaving the interface behind. Add 0.4 ml of TE-saturated phenol: chloroform (pg.) to the aqueous phase, vortex for 1 full minute, and centrifuge as in step 7. TE-saturated phenol: chloroform is prepared by mixing equal parts of TE buffer and phenol and allowing the phases to separate. Then one part of the lower, phenol, phase is mixed with one part of the chloroform: isoamyl alcohol (24:1).

9. Transfer the upper, aqueous phase to a fresh tube and repeat the phenol extraction as in step 7. If necessary, repeat this extraction several times until there is no visible material at the interface.

10. Transfer the upper, aqueous phase to a fresh tube and add 0.5 volume (200 ul) of 7.5 M ammonium acetate plus 2 volumes (1.2 ml) of ethanol. Mix and leave at 20° C. for 30 minutes to precipitate the phagemid DNA.

11. Centrifuge at 12,000×g for 5 minutes, remove the supernatant, carefully rinse the pellet with 70% ethanol, and centrifuge again for 2 minutes. Drain the tube and dry the pellet under vacuum. The pellet may be difficult to see.

12. Resuspend the DNA in 20 ul of $H_2O$. The amount of DNA present can be estimated by agarose gel electrophoresis of a 2 ul sample.

Two major bands are usually seen on 1% agarose gels run in Tris-acetate buffer: helper phage DNA and single-stranded plasmid DNA. In some preparations, a small amount of large chromosomal DNA may be present as well as some RNA resulting from cell lysis. In cases where the recombinant is the same size as the helper phage, it may be difficult to distinguish between the two species on a gel (M13K07 is 8.7 kb, R408 is 6.4 kb, and pSELECT-1™-Control is 5.6 kb). The helper band is usually more prominent if R408 is used. The presence of the helper phage DNA does not interfere with the mutagenesis reaction.

Mutagenesis Procedure

The mutagenesis reaction involves annealing of the ampicillin repair oligonucleotide (provided) and the mutagenic oligonucleotide to the ssDNA template, followed by synthesis of the mutant strand with T4 DNA polymerase. The heteroduplex DNA is then transformed into the repair minus E. coli strain BMH 71-18 mut S. Mutants are selected by overnight growth in the presence of ampicillin. Plasmid DNA is then isolated and transformed into the JM109 strain. Mutant, ampicillin resistant colonies may be screened by direct sequencing of the plasmid DNA.

The reagents to be supplied by the user are as follows:

Mutagenic oligonucleotide, phosphorylated

Sterile, deionized $H_2O$

DMSO, frozen in aliquots

Competent cells of the BMH 71-18 mut S and JM109 strains 18 mut S and JM109 strains Ampicillin LB medium LB plates+ampicillin[1]

Mini-prep lysis buffer

Potassium acetate solution, pH 4.8[2]

0.2N NaOH, 1% SDS (prepare fresh for each use)

TE buffer[3]

TE-saturated phenol/chloroform

Chloroform:isoamyl alcohol (24:1)

Ethanol (100% and 70%)

DNase-free RNase A[4]

[1]The LB plates+the ampicillin are prepared as follows: For one liter solution, 15 g agar is added to 1 liter of LB medium. The pH has been adjusted to 7.0 with NaOH, followed by autoclaving. The medium is allowed to cool to 55° C. before adding ampicillin (100 ug/ml final concentration). 30–35 ml of medium is poured into 85 mm petri dishes. If necessary, the surface of the medium is flamed with a Bunson burner to eliminate bubbles. The agar is then allowed to harden and can be stored at room temperature for one week (or at 4° C. for one month.)

[2]The potassium acetate solution is prepared by adding 11.5 ml of glacial acetic acid and 28.5 ml of water to 60 ml of 5M potassium acetate. This solution is 3M with respect to potassium and 5M with respect to acetate. The solution is stored at 4° C.

[3]The TE-buffer is prepared by mixing 10 mM Tris-HCl (pH 8.0) and 1 mM EDTA.

[4]The DNase-free RNase A is prepared by preparing a 10 mg/ml solution of RNase A in 10 mM Tris-HCl (pH 7.5), 15 mM NaCl. The mixture is heated at 100° C. for 15 minutes and cooled slowly to room temperature.

Annealing Reaction and Mutant Strand Synthesis

The amount of oligonucleotide required in this reaction may vary depending on the size and amount of the ssDNA template. The ampicillin repair oligonucleotide should be used at a 5:1 oligonuleotide:template ratio and the mutagenic oligonucleotide should be used at a 25:1 oligonu-leotide:template ratio. A typical reaction may contain 100 ng (0.05 pmol) of ssDNA. The protocol for this procedure is as follows:

1. Prepare the mutagenesis or control annealing reactions as described below.

| Mutagenesis Annealing Reaction | |
|---|---|
| Recombinant phagemid ssDNA | 0.05 pmol |
| Ampicillin repair oligonucleotide (2.2 ng/ul), phosphorylated | 0.25 pmol |
| Mutagenic oligonucleotide, phosphorylated (see following table) | 1.25 pmol |
| 10X Annealing buffer | 2 ul |
| Sterile $H_2O$ | to final volume 20 ul |

TABLE

| | Amount of Mutagenic Oligonucleotide Needed to Equal 1.25 pmol |
|---|---|
| Primer Length | ng of primer equal to 1.25 pmol |
| 17 mer | 7.0 ng |
| 20 mer | 8.3 ng |
| 23 mer | 9.5 ng |
| 26 mer | 10.8 ng |
| 29 mer | 12.0 ng |

| Control Annealing Reaction | | |
|---|---|---|
| pSELECT-1-Control phagemid ssDNA Ampicillin repair oligonucleotide | | (0.05 pmol) |
| (2.2 ng/ul), phosphorylated | 1 ul | (0.25 pmol) |
| lacZ control oligonucleotide | | |

-continued

Control Annealing Reaction

| (10.8 ng/ul), phosphorylated | 1 ul | (1.25 pmol) |
|---|---|---|
| 10X Annealing buffer | | 2 ul |
| Sterile H₂O | | to final volume 20 ul |

2. Heat the annealing reaction to 70° C. for 5 minutes and allow it to cool slowly to room temperature (15–20 minutes).

3. Place the annealing reaction on ice and add the following:

| 10X Synthesis buffer | 3 ul |
|---|---|
| T4 DNA polymerase (10 u/ul | 1 ul |
| T4 DNA ligase (2 u/ul | 1 ul |
| Sterile H₂O | 5 ul |
| | final volume 30 ul |

4. Incubate the reaction at 37° C. for 90 minutes to perform second strand synthesis and ligation.

Transformation into BMH 71-18 mut S

The protocol for this procedure is as follows:

1. Add 3 ul of DMSO to 200 ul of BMH 71-18 mut S competent cells, mix briefly, and then add the entire synthesis reaction from step 4 above. DMSO should be stored frozen in aliquots and not reused once thawed.

2. Let the cells sit on ice for 30 minutes.

3. For some strains, a heat shock at 42° C. for 1–2 minutes after the incubation on ice may increase transformation efficiency. However, it is optional.

4. Add 4 ml of LB medium and incubate at 37° C. for 1 hour to allow the cells to recover.

5. Add ampicillin to a final concentration of 125 ug/ml and incubate at 37° C. for 12–14 hours with shaking.

As a control to check the synthesis reaction, 1 ml of the culture can be removed after the one hour recovery step, spun down, resuspended in 50 ul of LB medium, and plated on LB plates containing 125 ug/ml ampicillin. This is a check for the presence of ampicillin resistant transformants; a second round of transformation is necessary before screening for mutants.

Plasmids Mini-Prep Procedure

This procedure is used to isolate pSELECT-1™ or pSELECT-1-Control plasmid DNA from the overnight culture of BMH 71-18 mut S (step 5, above). A yield of 1–3 ug of plasmid DNA may be expected. The protocol is as follows:

1. Place 1.5 ml of the overnight culture into a microcentrifuge tube and centrifuge at 12,000×g for 1 minute. The remainder of the overnight culture can be stored at 4° C.

2. Remove the medium by aspiration, leaving the bacterial pellet as dry as possible.

3. Resuspend the pellet by vortexing in 100 ul of ice cold miniprep lysis buffer (25 mM Tris-HCl, pH 8.0, 10 mM EDTA, 50 mM glucose).

4. Incubate for 5 minutes at room temperature.

5. Add 200 ul of a freshly prepared solution containing 0.2N NaOH, 1% SDS. Mix by inversion. DO NOT VORTEX. Incubate for 5 minutes on ice.

6. Add 150 ul of ice-cold potassium acetate solution, pH 4.8. Mix by inversion or gentle vortexing for 10 seconds. Incubate for 5 minutes on ice.

7. Centrifuge at 12,000×g for 5 minutes.

8. Transfer the supernatant to a fresh tube, avoiding the white precipitate.

9. Add 1 volume of TE-saturated phenol/chloroform. Vortex for 1 minute and centrifuge at 12,000×g for 5 minutes.

10. Transfer the upper, aqueous phage to a fresh tube and add 1 volume of chloroform:isoamyl alcohol (24:1). Vortex for 1 minute and centrifuge as in step 9.

11. Transfer the upper, aqueous phase to a fresh tube and add 2.5 volumes of 100% ethanol. Mix and allow to precipitate 5 minutes on dry ice.

12. Centrifuge at 12,000×g for 5 minutes. Rinse the pellet with 70% ethanol (prechilled) and dry the pellet under vacuum.

13. Dissolve the pellet in 50 ul of sterile deionized water. Add 0.5 ul of 100 ug/ml DNase-free RNase A and incubate for 5 minutes at room temperature.

14. The yield of plasmid DNA can be determined by electrophoresis on an agarose gel.

Transformation into JM109

The protocol for this procedure is as follows:

1. Add 3 ul of DMSO to 200 ul of JM109 competent cells, mix briefly, and add 0.05–0.10 ug of plasmid DNA from step 14 above.

2. Let the cells sit on ice for 30 minutes.

3. Optional step: A heat shock may be performed at this step.

4. Add 2 ml of LB medium and incubate at 37° C. for 1 hour to allow the cells to recover.

5. Divide the culture into two microcentrifuge tubes and spin for 1 minute in a microcentrifuge.

6. Pour off the supernatant and resuspend the cells in each tube in 50 ul of LB medium.

7. Plate the cells in each tube on an LB plate containing 125 ug/ml ampicillin and incubate at 37° C. for 12–14 hours.

Analysis of Transformants

The Altered Sites mutagenesis procedure generally produces greater than 50% mutants, so colonies may be screened by direct sequencing. A good strategy is to pick 10 colonies and start by sequencing 4 of these. If the mutation is located within 200–300 bases of either end of the DNA insert, the SP6 or T7 sequencing primers may be used for convenient priming of the sequencing reactions.

EXAMPLES

The following examples are provided as illustrative of the methods for generating the pSELECT vector in accordance with the invention, and the methods for site-specific in vitro mutagenesis in a DNA sequence coded by the pSELECT vector.

Example 1

Construction of pSELECT-1 pSELECT-1 is a cloning vector specifically constructed for use in in vitro mutagenesis. The vector is a hybrid of the plasmids pBR322 (Sutcliffe, J. G., 1979, *Cold Spring Harbor Symp. Quant. Biol.* 43, 77–90 and Peden, K. W. C., 1983, Gene 22, 277–280) and pGEM®-3Zf(+) (Promega Corporation, Madison, Wis.). The vector carries modified ampicillin and tetracycline resistance genes derived from pBR322 and in addition carries the polylinker and f1 replication origin from pGEM®-3Zf(+).

To construct pSELECT-1 the ampicillin resistance gene of pBR322 was inactivated by digesting the DNA with Pst I, blunting the ends using the Klenow fragment of DNA polymerase I and recircularizing the vector using T4 DNA ligase. (Maniatis, et al., 1982, *Molecular Cloning-A Laboratory Manual*, Cold Spring Harbor Laboratory, p. 114). This introduced a four-base frameshift which was checked by DNA sequencing and was found to make the vector ampicillin sensitive.

Figure 8:
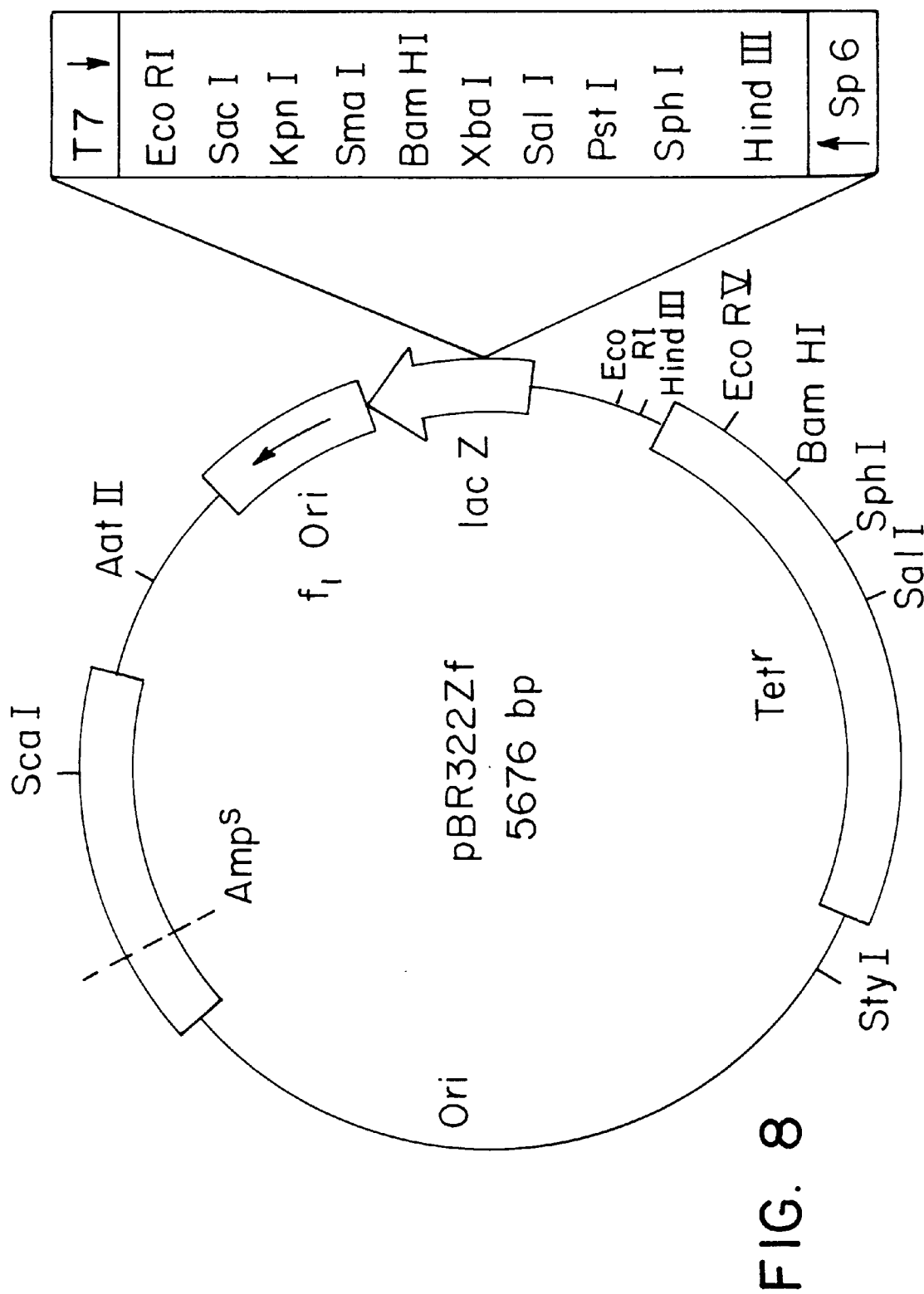
FIG. 8 is a partial restriction site and functional map of the plasmid pBR322ZF.

Ligation mixes were transformed into *E. coli* JM109 and plated on LB plates containing tetracycline. To clone the segments of pGEM®-3Zf(+) into this modified pBR322, the former was digested with Aat II and Afl III and the latter with Aat II and Eco R1 according the process described in Maniatis, et al., 1982, supra. The digests were mixed together and ligated for two hours, allowing the Aat II end of the pGEM®-3Zf(+) fragment to ligate to the Aat II end of the modified pBR322. The DNA ends were then blunted by filling in with Klenow and the ligation then allowed to proceed overnight. This step allows the recircularization of the recombinant plasmid by blunt end ligation of the filled Afl III and Eco R1 ends. The ligation mix was plated on LB plates containing tetracycline, IPTG and X-Gal and scored for tetracycline resistant blue colonies. To obtain a colony which is both tetracycline resistant and blue would indicate the successful cloning of the pGEM®-3Zf(+) Aat II-Afl III fragment (which carries the lac alpha peptide and hence confers blue color to JM109) into the tetracycline resistant modified pBR322 between the Aat II and Eco R1 sites. A blue tetracycline resistant colony was found and the structure of the resident plasmid was checked and found to be the correct fragment inserted into the modified pBR322. This plasmid was named pBR322ZF. Reference is made to FIG. 8 for a partial restriction site and functional map of the plasmid pBR322ZF. It was predicted that the Eco R1 site should have been reformed at the Afl III-Eco R1 junction, and in fact restriction mapping indicated that this was the case.

Figure 9:
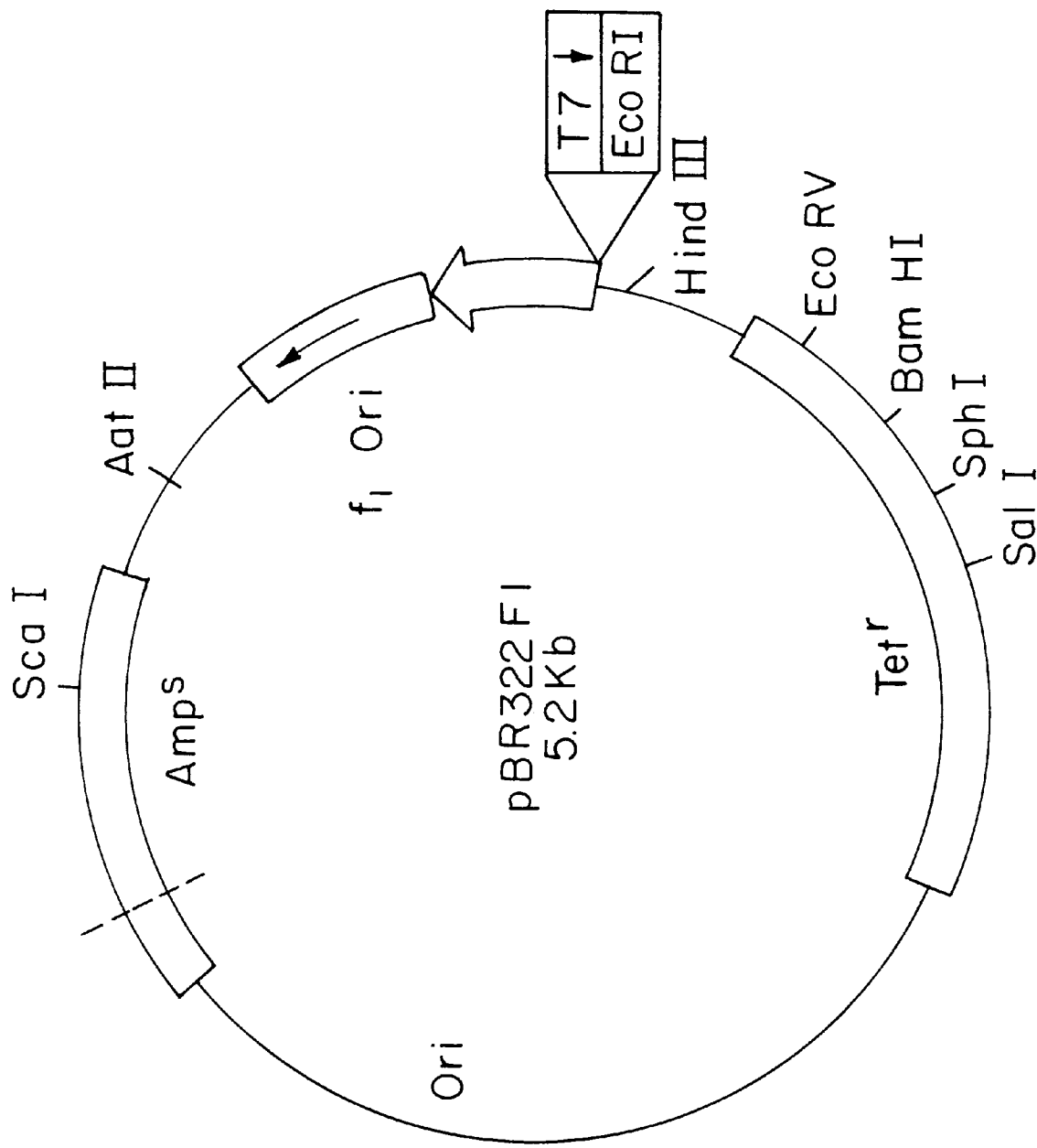
FIG. 9 is a partial restriction site and functional map of the plasmid pBR322F1.

Though the construct now contained the pGEM®-3Zf(+) polylinker, many of these sites were no longer unique. In particular, the Hind III, Bam H1, Sph I and Sal I sites in the linker were also present in the tetracycline resistance (tet) gene. In order to remove these sites from the tet gene, another derivative of pBR322 was constructed. In this case only the FI origin region from pGEM®-3Zf(+) was cloned into the ampicillin sensitive pBR322 derivative on an Aat II-Eco R1 fragment between the Aat II and Eco R1 sites on this vector. This allowed one to make ssDNA containing the tet gene and hence modify this gene by site-specific in vitro mutagenesis. This vector was named pBR322F1. Reference is made to FIG. 9 for a partial restriction site and functional map of the plasmid pBR322F1. Single-strand DNA was made from this vector by propagating the plasmid in *E. coli* NM522 and infecting with M13K07 helper phage. In vitro mutagenesis to remove the Hind III site was performed by hybridizing an oligonucleotide having the sequence pGCT-TATCATCGATTAGCTTTAATGCGG to the ssDNA. This oligonucleotide removes the Hind III site present in the tetracyline resistance gene promoter by changing the first A in the sequence AAGCTT to a T. About 0.1 ug of single-strand template was used and an oligonucleotide:vector ratio of about 15. The hybridization conditions were 25 mM Tris-HCl pH 7.3, 12 mM MgCl2 and 60 mM NaCl in a volume of 25 ul. The annealing reaction was heated to 70° C. for 5 minutes and then cooled to room temperature over the course of 15 minutes. Then all four deoxyribonucleotides (dATP, dCTP, dGTP, dTTP) were added to the reaction to a final concentration of 0.5 mM each, dATP to a final concentration of 1 mM, 10 units of T4 DNA polymerase (Promega Corp.) and 2 units of T4 DNA ligase (Promega Corp.). These additions increased the reaction volume to 35 ul. The fill in reaction was allowed to proceed for 90 minutes at 37° C. at which point the entire reaction was transformed into competent BMH71-18 mut S *E. coli* and the transformation mixture added to a 50 ml LB culture containing 15 ug/ml tetracycline and the culture grown up overnight.

Plasmid DNA was then prepared from this culture using a mini-prep procedure, the DNA was restricted with Hind III (to select for those mutants missing the Hind III site), transformed into *E. coli* JM109 and the cells plated on LB plates containing 15 ug/ml tetracycline. Two tetracyline resistant colonies were isolated and plasmid DNA prepared from these isolates. Restriction enzyme digestion indicated that both isolates had in fact deleted the Hind III site.

To delete the Bam H1, Sph I and Sal I sites from the tetracycline resistance gene, oligonucleotides were designed which removed each restriction site while keeping the amino acid sequence of the tet protein unchanged. The respective oligonucleotides used were pCCCGTCCTGTGGATTCTCTACGCCGG, pGGCGC-CATCTCCTTACATGCACCATTCCTTGCG and pTCG-CATAAGGGAGAGCGCCGACCCATGCCCTTG. In each case the mutagenesis procedure was followed essentially as above and basically involved a hybridization, an in vitro fill in, a transformation, a plasmid preparation, a restriction enzyme recut and a retransformation. This completed the engineering of the tetracyline resistance gene so that it would be useful when incorporated into the mutagenesis vector.

To transfer the modified tet gene into pBR322ZF, the gene was excised on a Cla I-Sty I fragment, gel purified and cloned into pBR322ZF between the Cla I and Sty I sites. Next, one of the two Eco R1 sites in the resulting vector was removed. The site removed was the one outside the polylinker and it was destroyed by partial Eco R1 digestion, filling with Klenow and religating, followed by restriction enzyme digestion to map which site was removed from isolates which cut only once with Eco R1. The resulting vector was named pSELECT-1.

Example 2

In Vitro Mutagenesis to Ampicillin Resistance Using pSELECT-1

To revert pSELECT-1 to ampicillin resistance, single-stranded DNA was prepared from the vector in the host JM109 using R408 helper phage according to standard procedures described in pGEM® Single Strand System Technical Manual. (supra). The single-stranded DNA (about 0.1 ug in a volume of 20 ul) was hybridized to an oligonucleotide having the sequence pGTTGCCATTGCTG-CAGGCATCGTGGTG which restores those four bases to the sequence of the ampicillin resistance gene which had been modified by the removal of the Pst I site. The oligonucleotide:vector ratio was about 10:1 and hybridization was performed by heating to 70° C. for 5 minutes and then allowing the reaction to cool to room temperature over the course of 15 minutes. Following the hybridization the fill-in reaction was performed by adding all four deoxynucleotides to 0.5 mM, rATP to 1 mM and 10 units of T4 DNA polymerase and 4 units of T4 DNA ligase. The extension reaction was then allowed to proceed for 90 minutes at 37° C. The reaction was then transformed into competent *E. coli* BMH71-18 mut S and plated on LB plates containing ampicillin. The reaction gave rise to about 1000 ampicillin resistant colonies.

Example 3

Couplina Ampicillin Repair to a Second Mutation

In order to demonstrate the ability to link the ampicillin repair oligonucleotide to a second mutagenic oligonucleotide at high frequency, single-stranded pSELECT DNA was hybridized to both the ampicillin repair oligonucleotide (described in Example 2) and a second mutagenic oligonucleotide having the sequence pTCTAGAGTCGAC-CCAGGCATGCAAGCT. This second oligonucleotide hybridizes to the lac alpha-peptide region in the vector and disrupts the reading frame of the peptide. Disruption of the reading frame results in a change of phenotype from blue to white. The fraction of ampicillin resistant colonies which are also white (instead of the wild-type blue) gives the mutagenesis frequency.

Following hybridization and extension reactions as described in Example 2, the reaction mixture was transformed into BMH71-18 mut S and the strain allowed to grow into a culture in the presence of 100 ug/ml ampicillin. Plasmid DNA was then prepared from this culture and retransformed, this time into *E. coli* JM109.

The resulting colonies when plated on ampicillin plates containing IPTC and X-gal resulted in about 80% whites and 20% blues. The second mutation (the blue to white change) had apparently been coupled with 80% efficiency to the ampicillin repair, a selectable marker. When mutagenesis was performed using only the one lac disrupt oligonucleotide (unselected), an efficiency of only about 4% (4% white colonies) was observed. When the ampicillin repair oligonucleotide alone was used and the bacteria plated on ampicillin/IPTC/X-gal, only blue colonies resulted. In order to express the white phenotype, it was necessary to go through two rounds of transformation because the blue color is dominant and contributed by plasmids carried in the same cell as the mutants and derived from replication of the parental DNA strand.

Example 4

Construction and Use of pSELECT-1 Control Plasmid To Study Frequency of Restoration of Function Mutation Because the white to blue change described in Example 3 is an example of a loss of function mutation and could have resulted from changes other than the one predicted, it was felt important to test the ability to select for a restoration of function mutation using the pSELECT vector. Therefore, a derivative of pSELECT was created which has a white phenotype and was derived from pSELECT by cutting with Pst I, blunting the ends with Klenow and religating. These operations resulted in the removal of four nucleotide bases and frame-shifting the lac alpha peptide, resulting in a white phenotype.

The ability to couple ampicillin resistance to a change from a white to a blue phenotype was examined. The ampicillin repair oligonucleotide was hybridized to ssDNA from the modified pSELECT vector along with an oligonucleotide of sequence pTAGAGTCGACCTGCAGGCAT-GCAAGC. This second oligonucleotide restores the Pst I site and converts the vector from white to blue by restoring the reading frame of the alpha peptide. Mutagenesis was performed as described in the above examples. Following two rounds of transformation, cells were plated and resulted in 88% blue colonies and 12% white. Again, a high frequency of mutagenesis was obtained using the vector, this time for a restoration of function.

Example 5

Mutating a Foreign Gene Insert

In order to test the efficiency of mutagenesis using an insert in the pSELECT vector, the gene coding for chloramphenicol acetyl transferase (CAT) was cloned into a modified pSELECT vector, rendered non-functional by introducing a four-base deletion, and then mutated back to functionality using an oligonucleotide which was linked in the normal fashion to the ampicillin repair oligonucleotide. First, the Eco RI site in the MCS of pSELECT was deleted by cutting with Eco RI, filling the ends with Klenow and then religating. An 800 base pair Hind III fragment comprising a promoter-less CAT gene (Pharmacia Corp.) was then cloned into the Hind III site of the modified vector and the transformed cells spread on plates containing chloramphenicol. Four isolates were examined and in each case the orientation of the insert was found to be such that sense transcription of the CAT gene was directed by the lac promoter on the vector. The cloned CAT gene was then inactivated by cutting at the internal Eco RI site, filling the ends with Klenow and then religating. This introduced a four-base insertion into the coding region of the gene, frameshifting the gene product and rendering it inactive. The efficiency of correcting this insertion with the appropriate oligonucleotide was examined. In vitro mutagenesis was performed using single stranded DNA from the construct, the ampicillin repair oligonucleotide and an oligonucleotide which restored the natural sequence to the CAT gene. Of sixty ampicillin resistant colonies recovered from the mutagenesis, thirty-three were found also to grow on chloramphenicol, indicating a mutation frequency in a restoration of function insertion mutagenesis of fifty-five percent (55%). This frequency is high enough to be able to readily identify mutants simply by sequencing a few clones.

Example 6

Performin Multiple Mutations at Once

The mutagenesis method was also tested for the ability to select for the incorporation of two different mutations at the same time. In this case the lac Z repair oligo (white to blue, Example 4) was used with pSELECT-Control single stranded DNA along with the amp repair oligo and a third oligo which was designed to restore the deleted Bam HI site within the teracycline resistance gene. Eighty-six percent (86%) blue colonies were obtained. Fifteen of these were checked for the incorporation of the new Bam HI site and all fifteen were found to have incorporated this new site. Thus, it is possible to use the system to create more than one change at once. This ability obviates the need to reclone into the ampicillin sensitive vector if it is desired to create more than one mutation within a given target gene.

In is understood that the invention is not limited to the particular embodiments specifically disclosed herein as exemplary, but embraces such modified forms thereof as come within the scope of the following claims.

What is claimed is:

1. A method for site-specific in vitro mutagenesis in a DNA sequence comprising:
   a) forming a single-stranded DNA template from a double-stranded plasmid DNA vector which comprises (i) the DNA sequence to be mutated, (ii) an inactive first genetic marker which can be restored to functional expression, (iii) an active second genetic marker which is different from the first genetic marker, and (iv) a replication origin of a filamentous bacteriophage;
   b) forming a heteroduplex by hybridizing at least one mismatched mutagenic oligonucleotide and a restoration oligonucleotide to the single-stranded DNA template formed in step a), wherein the restoration oligonucleotide can activate the functional expression of the first genetic marker;

c) converting the heteroduplex to a full-length double-stranded DNA molecule;

d) transforming the double-stranded DNA molecule of step c) into an *E. coli* host; and e) plating the transformants obtained in step d) on a medium containing a component that allows screening or selection for transformants carrying a functional first genetic marker.

2. The method of claim 1 wherein the heteroduplex is converted to a full length double-stranded DNA molecule by adding the deoxynucleotides dATP, dCTP, dGTP and dTTP in the presence of T4 DNA polymerase and T4 DNA ligase.

3. The method of claim 1 further comprising identifying after step e) the double-stranded DNA molecules of step c) which carry a functional first genetic marker.

4. The method of claim 3 wherein after step e) the double-stranded DNA molecules of step c) are examined by DNA sequencing techniques for the presence of a mutation corresponding to the at least one mutagenic mismatched oligonucleotide.

5. The method of claim 1 wherein the first genetic marker is a nutritional marker.

6. The method of claim 1 wherein the first genetic marker is a marker for leucine biosynthesis.

7. The method of claim 1 wherein the first genetic marker, when functional, varies the color of the host.

8. The method of claim 1 wherein, in the double-stranded DNA vector, the replication origin of a filamentous bacteriophage is an f1 replication origin.

9. The method of claim 8 wherein the double-stranded DNA vector further comprises a polylinker region in which the DNA sequence to be mutated is located.

10. The method of claim 9 wherein the vector comprises the following components:

a) an inactivated ampicillin resistance gene from the plasmid pBR322;

b) a tetracycline resistance gene from the plasmid pBR322;

c) a polylinker region from the plasmid pGEM®-3Zf(+); and d) an f1 replication origin from the plasmid pGEM®-3Zf (+).

11. The method of claim 9 wherein the first genetic marker is an antibiotic resistance marker.

12. The method of claim 11 wherein the antibiotic against which the first genetic marker, when functional, provides resistance is selected from the group consisting of ampicillin, tetracycline, neomycin, streptomycin, and chloramphenicol.

13. The method of claim 12 wherein the antibiotic against which the first genetic marker, when functional, provides resistance is ampicillin.

14. The method of claim 13 wherein the first genetic marker, when inactive, is the inactive ampicillin resistance gene of plasmid pBR322 which lacks the four base pairs, in thesequence 5'-dTGCA, from the PstI site in the active ampicillin resistance gene of the plasmid.

15. The method of claim 14 wherein the second genetic marker is a tetracycline resistance gene.

16. The method of claim 15 wherein the tetracycline resistance gene is a modified tetracycline resistance gene of plasmid pBR322, which modified gene has no recognition site for the restriction enzymes HindIII, BamHI, SphI and SalI.

17. The method of claim 16 wherein the polylinker region is of plasmid pGEM®-3Zf(+).

18. The method of claim 17 wherein the f1 replication origin is of plasmid pGEM®-3Zf(+).

19. The method of claim 18 wherein the double-stranded DNA vector used in step a) is pSELECT-1 as shown in FIG. 4.

20. The method of claim 16 wherein the f1 replication origin is of plasmid pGEM®-3Zf(+).

21. The method of claim 13 wherein the second genetic marker is a tetracycline resistance gene.

22. The method of claim 12 wherein the second genetic marker provides resistance against an antibiotic selected from the group consisting of ampicillin, tetracycline, neomycin, streptomycin, and chloramphenicol and different from the antibiotic against which the first genetic marker, when functional, provides resistance.

23. The method of claim 12 wherein the second genetic marker is a tetracycline resistance gene.

24. The method of claim 11 wherein the second genetic marker is an antibiotic resistance marker.

25. The method of claim 9 wherein the second genetic marker is an antibiotic resistance marker.

26. The method of claim 1 wherein the double-stranded DNA vector further comprises a polylinker region in which the DNA sequence to be mutated is located.

27. The method of claim 1 wherein the first genetic marker, prior to activation to functional expression, is inactive due to a frame-shift mutation.

28. The method of claim 1 wherein the first genetic marker is an antibiotic resistance marker.

29. The method of claim 28 wherein the antibiotic against which the first genetic marker, when functional, provides resistance is selected from the group consisting of ampicillin, tetracycline, neomycin, streptomycin, and chloramphenicol.

30. The method of claim 29 wherein the antibiotic against which the first genetic marker, when functional, provides resistance is ampicillin.

31. The method of claim 30 wherein the first genetic marker, when inactive, is the inactive ampicillin resistance gene of plasmid pBR322 which lacks the four base pairs, in the sequence 5'-dTGCA, from the PstI site in the active ampicillin resistance gene of the plasmid.

32. The method of claim 31 wherein the second genetic marker is a tetracycline resistance gene.

33. The method of claim 32 wherein the tetracycline resistance gene is a modified tetracycline resistance gene of plasmid pBR322, which modified gene has no recognition site for the restriction enzymes HindIII, BamHI, SphI and SalI.

34. The method of claim 30 wherein the second genetic marker is a tetracycline resistance gene.

35. The method of claim 29 wherein the second genetic marker provides resistance against an antibiotic selected from the group consisting of ampicillin, tetracycline, neomycin, streptomycin, and chloramphenicol and different from the antibiotic against which the first genetic marker, when functional, provides resistance.

36. The method of claim 29 wherein the second genetic marker is a tetracycline resistance gene.

37. The method of claim 28 wherein the second genetic marker is an antibiotic resistance marker.

38. The method of claim 1 wherein the second genetic marker is an antibiotic resistance marker.

39. A double-stranded plasmid DNA vector for use in site-specific mutagenesis of a DNA sequence which comprises (i) an inactive first genetic marker which can be restored to functional expression, (ii) an active second genetic marker which is different from the first genetic marker, (iii) a site for insertion of a DNA sequence to be mutagenized, and (iv) a replication origin of a filamentous bacteriophage, wherein said inactive first genetic marker can be restored to functional expression by a restoration oligonucleotide which can hybridize to one strand of the DNA vector thereby activating functional expression of the first genetic marker.

40. The vector of claim 39 wherein the first and second genetic markers are antibiotic resistance markers.

41. The vector of claim 40 wherein the first genetic marker is for a first antibiotic selected from the group consisting of ampicillin, tetracycline, neomycin, streptomycin, and chloramphenicol and the second genetic marker is for a second antibiotic which is different from the first antibiotic and selected from the group consisting of ampicillin, tetracycline, neomycin, streptomycin, and chloramphenicol.

42. The vector of claim 41 wherein the first genetic marker is an ampicillin resistance gene.

43. The vector of claim 42 wherein the inactivated first genetic marker is the inactive ampicillin resistance gene of plasmid pBR322 which lacks the four base pairs, in the sequence 5'-dTGCA, from the PstI site in the active ampicillin resistance gene of the plasmid.

44. The vector of claim 43 wherein the second genetic marker is a tetracycline resistance gene.

45. The vector of claim 44 wherein the tetracycline resistance gene is a modified tetracycline resistance gene of pBR322, which modified gene has no recognition site for the restriction enzymes HindIII, BamHI, SphI and SalI.

46. The vector of claim 45 wherein the f1 replication origin is a f1 replication origin of the plasmid pGEM®-3Zf (+).

47. The vector of claim 46 wherein the polylinker is a polylinker region of the plasmid pGEM®-3Zf(+).

48. The vector of claim 45 wherein the polylinker is a polylinker region of the plasmid pGEM®-3Zf(+).

49. The vector of claim 42 wherein the second genetic marker is a tetracycline resistance gene.

50. The vector of claim 49 wherein the tetracycline resistance gene is a modified tetracycline resistance gene of plasmid pBR322, which modified gene has no recognition site for the restriction enzymes HindIII, BamHI, SphI and SalI.

51. The double-stranded DNA vector of claim 39 wherein the inactivity of the first genetic marker is due to a frameshift mutation.

52. The double-stranded DNA vector of claim 39 wherein the replication origin of a filamentous bacteriophage is an f1 replication origin.

53. The double-stranded DNA vector of claim 39 which further comprises a polylinker region which comprises a site for insertion of a DNA sequence to be mutagenized.

54. The double-stranded DNA vector of claim 53 wherein the replication origin of a filamentous bacteriophage is an f1 replication origin.

55. The double-stranded DNA vector of claim 54 wherein the inactivity of the first genetic marker is due to a frameshift mutation.

56. The vector of claim 55 wherein the first genetic marker is an antibiotic resistance marker for an antibiotic selected from the group consisting of ampicillin, tetracycline, neomycin, streptomycin, and chloramphenicol.

57. The vector of claim 55 wherein the second genetic marker is an antibiotic resistance marker for an antibiotic selected from the group consisting of ampicillin, tetracycline, neomycin, streptomycin, and chloramphenicol.

58. The vector of claim 55 wherein the first and second genetic markers are antibiotic resistance markers.

59. The vector of claim 58 wherein the first genetic marker is for a first antibiotic selected from the group consisting of ampicillin, tetracycline, neomycin, streptomycin, and chloramphenicol and the second genetic marker is for a second antibiotic which is different from the first antibiotic and selected from the group consisting of ampicillin, tetracycline, neomycin, streptomycin, and chloramphenicol.

60. The vector of claim 59 wherein the first genetic marker is an ampicillin resistance gene.

61. The vector of claim 60 wherein the inactivated first genetic marker is the inactive ampicillin resistance gene of plasmid pBR322 which lacks the four base pairs, in the sequence 5'-dTGCA, from the PstI site in the active ampicillin resistance gene of the plasmid.

62. The vector of claim 61 wherein the second genetic marker is a tetracycline resistance gene.

63. The vector of claim 62 wherein the tetracycline Resistance gene is a modified tetracycline resistance gene of pBR322, which modified gene has no recognition site for the restriction enzymes HindIII, BamHI, SphI and SalI.

64. The vector of claim 63 wherein the f1 replication origin is a f1 replication origin of the plasmid pGEM®-3Zf (+).

65. The vector of claim 64 wherein the polylinker is a polylinker region of the plasmid pGEM®-3Zf(+).

66. The vector of claim 65 which is pSELECT-1 as shown in FIG. 4.

67. The vector of claim 63 wherein the polylinker is a polylinker region of the plasmid pGEMO-3Zf(+).

68. The vector of claim 60 wherein the second genetic marker is a tetracycline resistance gene.

69. The vector of claim 68 wherein the tetracycline resistance gene is a modified tetracycline resistance gene of plasmid pBR322, which modified gene has no recognition site for the restriction enzymes HindIII, BamHI, SphI and SalI.

70. The vector of claim 55 wherein the f1 replication origin is a f1 replication origin of the plasmid pGEM®-3Zf (+).

71. The vector of claim 54 wherein the f1 replication origin is a f1 replication origin of the plasmid pGEM®-3Zf (+).

72. The vector of claim 54 wherein the polylinker is a polylinker region of the plasmid pGEM®-3Zf(+).

73. The vector of claim 53 wherein the polylinker is a polylinker region of the plasmid pGEM®-3Zf(+).

74. The vector of claim 39 wherein the first genetic marker is an antibiotic resistance marker for an antibiotic selected from the group consisting of ampicillin, tetracycline, neomycin, streptomycin, and chloramphenicol.

75. The vector of claim 39 wherein the second genetic marker is an antibiotic resistance marker for an antibiotic selected from the group consisting of ampicillin, tetracycline, neomycin, streptomycin, and chloramphenicol.

76. A kit for conducting site-specific in vitro mutagenesis in a DNA sequence, comprising:
   a) a container containing a double-stranded DNA plasmid vector which comprises (i) an inactive first genetic marker which can be restored to functional expression, (ii) an active second genetic marker, (iii) a site for insertion of the DNA sequence to be mutagenized and (iv) a replication origin of a filamentous bacteriophage;

b) a container containing helper phage to produce single-stranded DNA from the double-stranded DNA plasmid vector of container a);

c) a container containing a restoration oligonucleotide which can activate the functional expression of the first genetic marker of the double-stranded DNA vector of container a); and d) a container containing an *E. coli* host which can be used to select for the mutagenized DNA sequence.

77. The kit of claim 76 wherein, in the DNA vector of container a), the origin of replication of a filamentous bacteriophage is an f1 replication origin.

78. The kit of claim 77 wherein the DNA vector of container a) comprises a polylinker region which comprises a site for insertion of the DNA sequence to be mutagenized.

79. A kit according to claim 77 wherein the DNA vector of container a) is a pSELECT vector.

80. A kit according to claim 79 wherein the pSELECT vector is pSELECT-1 as shown in FIG. 4.

81. The kit of claim 76 wherein the DNA vector of container a) comprises a polylinker region which comprises a site for insertion of the DNA sequence to be mutagenized.

* * * * *

UNITED STATES PATENT AND TRADEMARK OFFICE
CERTIFICATE OF CORRECTION

PATENT NO. : 5,955,363
DATED : September 21, 1999
INVENTOR(S) : Martin K. Lewis et al.

It is certified that error appears in the above-identified patent and that said Letters Patent is hereby corrected as shown below:

Column 3,
Line 60, delete "Vandevar" and insert in its place -- Vandeyar --.

Column 7,
Line 44, delete "pSELECT-1plasmid" and insert in its place -- pSELECT-1 plasmid --.

Column 9,
Line 66, delete "30" before the word "extension".

Column 11,
Lines 56-57, 58-59 and 61, delete "pSELECT$^{TM}$" and insert in its place -- pSELECT-1 --.
Lines 58-59, "Cloning into the pSELECT-1 Vector" should be formatted as a heading.

Column 12,
Lines 14 and 15, delete both occurrences of "pSELECT$^{TM}$" and substitute for each of them -- pSELECT-1 --.
Line 38, delete both occurrences of "pSELECT-1$^{TM}$" and substitute for each of them -- pSELECT-1 --.

Column 13,
Line 32, delete "pSELECT-1$^{TM}$" and insert in its place -- pSELECT-1 --.

Column 15,
Line 42, delete "pSELECT-1$^{TM}$" and insert in its place -- pSELECT-1 --.
Line 43, delete "pSELECT-1-Control" and insert in its place -- pSELECT-Control --.

Column 18,
Line 64, delete "Couplina" as the first word in the title and insert in its place -- Coupling --.

Column 19,
Line 35, in the heading for Example 4, delete "1 Control" and insert in its place -- 1-Control --.

Column 20,
Line 34, delete "Performin" and insert in its place -- "Performing" --.

UNITED STATES PATENT AND TRADEMARK OFFICE
CERTIFICATE OF CORRECTION

PATENT NO. : 5,955,363
DATED : September 21, 1999
INVENTOR(S) : Martin K. Lewis et al.

It is certified that error appears in the above-identified patent and that said Letters Patent is hereby corrected as shown below:

Column 21, claim 14,
Line 59, delete "thesequence" and insert in its place -- the sequence --.

Column 24, claim 63,
Line 23, delete "Resistance" and insert in its place -- resistance --.

Column 24, claim 67,
Line 34, delete "pGEMO" and insert in its place -- pGEM® --.

Signed and Sealed this

Twenty-sixth Day of March, 2002

Attest:

*Attesting Officer*

JAMES E. ROGAN
*Director of the United States Patent and Trademark Office*